United States Patent [19]

Ohta et al.

[11] Patent Number: 5,447,693
[45] Date of Patent: Sep. 5, 1995

[54] DEODORANT EQUIPMENT FOR AIR CONDITIONER

[75] Inventors: Masatoshi Ohta, Nabari; Takahiro Ueno, Mie; Fumihiro Ito, Shiga; Masami Matsunaga; Kazuo Hashimoto, both of Mie, all of Japan

[73] Assignee: Matsushita Refrigeration Company, Japan

[21] Appl. No.: 220,870

[22] Filed: Mar. 31, 1994

[30] Foreign Application Priority Data

| Apr. 2, 1993 | [JP] | Japan | 5-076639 |
| Apr. 14, 1993 | [JP] | Japan | 5-087138 |
| Nov. 19, 1993 | [JP] | Japan | 5-290817 |

[51] Int. Cl.⁶ ............................ B01D 51/10
[52] U.S. Cl. ............................ 422/122; 62/70; 237/12.3 A; 422/109; 422/116; 422/124; 422/125; 422/173; 422/174; 422/177
[58] Field of Search ............ 422/122, 124, 125, 177, 422/173, 174, 108–109, 116; 62/70; 237/12.31 A

[56] References Cited

U.S. PATENT DOCUMENTS

| 2,988,432 | 6/1961 | Long | 422/122 |
| 3,691,346 | 9/1972 | Dyre et al. | 422/122 X |
| 3,779,710 | 12/1973 | Burstein et al. | 422/122 X |
| 4,948,567 | 8/1990 | Atarashiya | 422/4 X |
| 5,230,220 | 7/1993 | Kang et al. | 422/121 X |
| 5,278,113 | 1/1994 | Ono et al. | 502/66 |
| 5,291,742 | 3/1994 | Kawatani et al. | 422/125 X |
| 5,347,820 | 9/1994 | In Gweon | 422/122 X |

FOREIGN PATENT DOCUMENTS 1-169247  4/1989  Japan .

*Primary Examiner*—Robert J. Warden
*Assistant Examiner*—Krisanne M. Thornton
*Attorney, Agent, or Firm*—Parkhurst, Wendel & Rossi

[57] ABSTRACT

A deodorant equipment for an air conditioner includes a heater. A fin covers at least a part of an effective heating area of a surface of the heater. The fin has a radiator portion extending along a longitudinal direction of the heater. A vitreous coating film covers at least a part of an outer surface of the fin. A catalyst layer includes an absorption member and a catalyst. The absorption member absorbs odor components of air. The absorption member releases the odor components when being heated. The catalyst oxidizes and decomposes odor components when being heated.

36 Claims, 16 Drawing Sheets

DEODORANT EQUIPMENT FOR AIR CONDITIONER

BACKGROUND OF THE INVENTION

1. Field of the Invention

This invention generally relates to a deodorant equipment or a deodorizing apparatus. This invention specifically relates to a deodorant equipment for an air conditioner.

2. Description of the Prior Art

It is well-known to use activated charcoal to absorb and deodorize stinking gas. Japanese published unexamined patent application 1-169247 discloses an air conditioner having an apparatus for generating ozone gas. The ozone generating apparatus is used as a deodorant equipment. Specifically, the ozone gas is operative to oxidize and decompose stinking substances into odorless (non-stinking) substances.

Typical stinking substances are ammonia, fatty acid, unsaturated hydrocarbons, nitrogen-containing organic compounds, sulfur-containing organic compounds, and mercaptan which result from human excretion and decomposition of foods.

In a prior-art deodorant equipment using activated charcoal, it is necessary to periodically replace activated charcoal to maintain the deodorizing function for a long period.

A prior-art deodorant equipment using ozone gas needs a special device which controls the ozone concentration in a given range optimal for the deodorizing function. There are some stinking substances which can not be decomposed by ozone. Generally, an apparatus for generating ozone gas has a significantly limited life.

SUMMARY OF THE INVENTION

It is an object of this invention to provide an improved deodorant equipment.

A first aspect of this invention provides a deodorant equipment for an air conditioner which comprises a heater; a fin covering at least a part of an effective heating area of a surface of the heater and having a radiator portion extending along a longitudinal direction of the heater; a vitreous coating film covering at least a part of an outer surface of the fin; and a catalyst layer including an absorption member and a catalyst, the absorption member absorbing odor components of air and releasing the odor components when being heated, the catalyst oxidizing and decomposing odor components when being heated.

A second aspect of this invention provides a deodorizing apparatus comprising an absorbent for absorbing odor components of air, and releasing the absorbed odor components when being heated; a catalyst for decomposing the odor components released from the absorbent; and a heater for heating the absorbent.

A third aspect of this invention provides a deodorizing apparatus placed in an air conditioner which comprises means for detecting whether or not the air conditioner is operating absorbent for absorbing odor components of air, and releasing the absorbed odor components when being heated; a catalyst for decomposing the odor components released from the absorbent; and means connected to the detecting means for periodically heating the absorbent while the detecting means continues to detect that the air conditioner is operating.

A fourth aspect of this invention provides a deodorizing apparatus placed in an air conditioner which comprises means for detecting a change of operation of the air conditioner from a cooling mode; absorbent for absorbing odor components of air, and releasing the absorbed odor components when being heated; a catalyst for decomposing the odor components released from the absorbent; and means connected to the detecting means for heating the absorbent after the detecting means detects a change of operation of the air conditioner from the cooling mode.

DESCRIPTION OF THE FIRST PREFERRED EMBODIMENT

Figure 1:
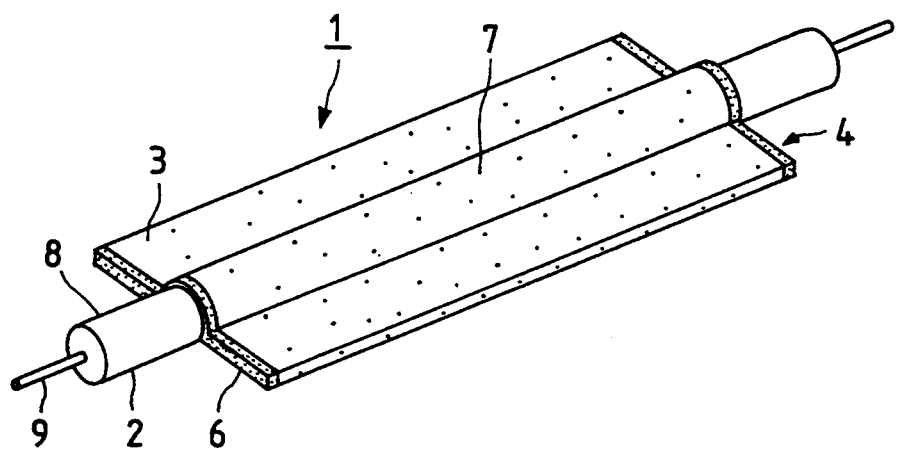
FIG. 1 is a perspective view of a deodorant equipment according to a first embodiment of this invention.
Figure 2:
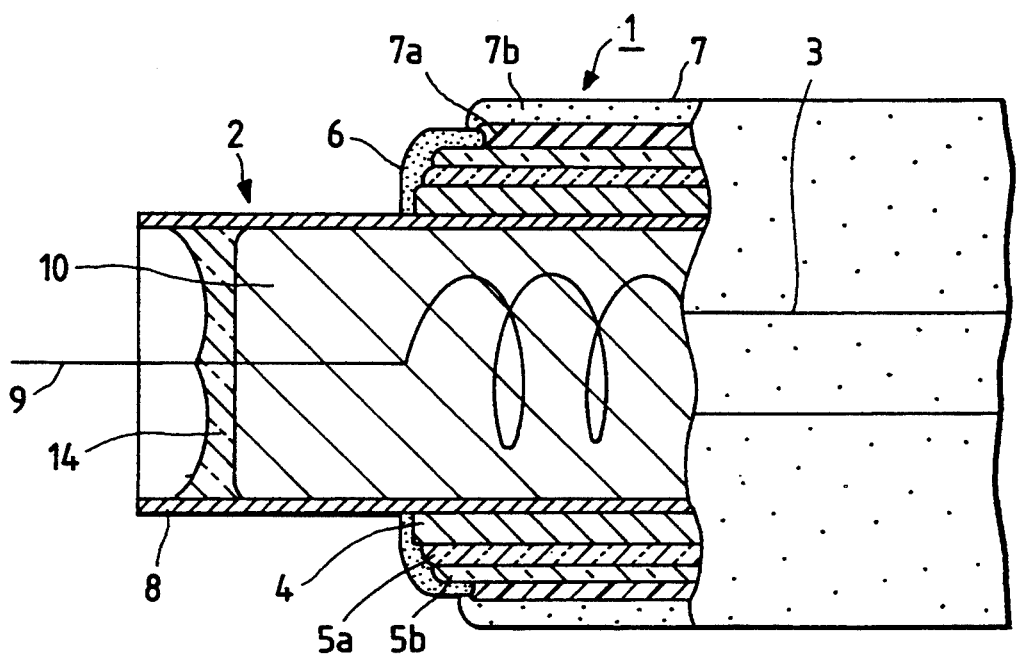
FIG. 2 is a side view, partially in cross section, of the deodorant equipment of FIG. 1.

With reference to FIGS. 1 and 2, a deodorant equipment 1 includes a metal tube heater 2, a fin arrangement 4, a vitreous coating film 5, protective layers 6, and a catalyst layer 7.

The metal tube heater 2 includes a metal tube 8 and an electric resistance wire (a heating wire) 9. The electric resistance wire 9 extends through the interior of the metal tube 8. The electric resistance wire 9 is separated from and supported on the metal tube 8 by electrically-insulating and thermally-conducting material 10 which fills the interior of the metal tube 8.

The fin arrangement 4 is made of aluminized steel. The fin arrangement 4 includes a tubular base, and radiators 3 projecting outward from the tubular base. The base of the fin arrangement 4 entirely or partially covers an effective heating region of surfaces of the metal tube heater 2. The radiators 3 of the fin arrangement 4 are integral with the base of the fin arrangement 4. The radiators 3 are diametrically opposed to each other. The radiators 3 have a rectangular flat configuration. The radiators 3 extend along the longitudinal direction (the axial direction) of the metal tube heater 2.

The vitreous coating film 5 covers at least a part of outer surfaces of the fin arrangement 4. The vitreous coating film 5 is made of glass material or similar material. The vitreous coating film 5 has a laminate of an inner layer 5a and an outer layer 5b. The inner layer 5a has a relatively dense texture or organization. The outer layer 5b has a relatively coarse texture or organization. The outer layer 5b is rich in ceramics.

The protective layers 6 are made of a heat-resisting and rust-preventing paint. The protective layers 6 cover respective ends of the fin arrangement 4 in the length direction (the longitudinal direction) thereof. The protective layers 6 also cover ends of the vitreous coating film 5.

The catalyst layer 7 is formed on the vitreous coating film 5. The catalyst layer 7 contains at least activated alumina, silica, zeolite, and platinum group metal. The catalyst layer 7 has a laminate of an inner layer 7a and an outer layer 7b. The inner layer 7a is an absorption layer containing activated alumina, silica, and zeolite. The outer layer 7b is a metal catalyst layer 7b containing platinum group metal. The outer layer 7b is porous so that air and gas can flow therethrough.

The deodorant equipment 1 is manufactured as follows. First, an electric resistance wire or a heating wire 9 is inserted into a metal tube 8. Then, the metal tube 8 is charged with electrically-insulating and thermally-conducting material 10 such as magnesium oxide to fabricate a metal tube heater 2. The electrically-insulating and thermally-conducting material 10 separates the electric resistance wire 9 from the metal tube 8, and also supports the electric resistance wire 9 on the metal tube 8.

Figure 3:
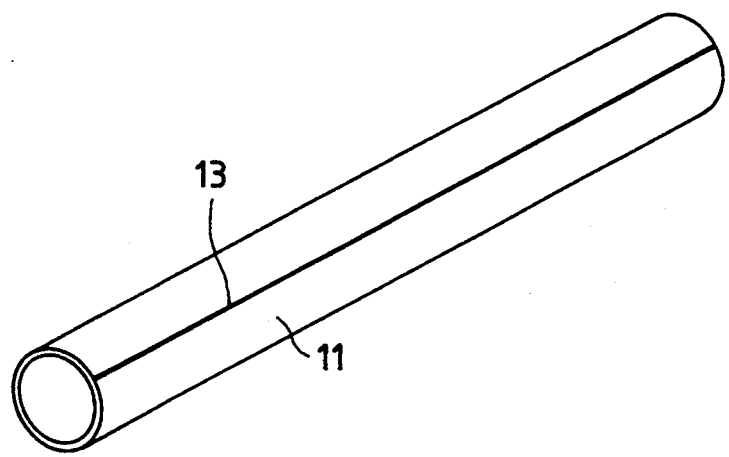
FIG. 3 is a perspective view of a metal tube used for a fin arrangement in the deodorant equipment of FIG. 1.

During a subsequent period, as shown in FIG. 3, a rectangular flat plate of aluminized steel is rounded and made into a tube 11, and adjacent edges 13 of walls of the tube 11 are welded together. In this way, an aluminized steel tube 11 is made.

Figure 4:
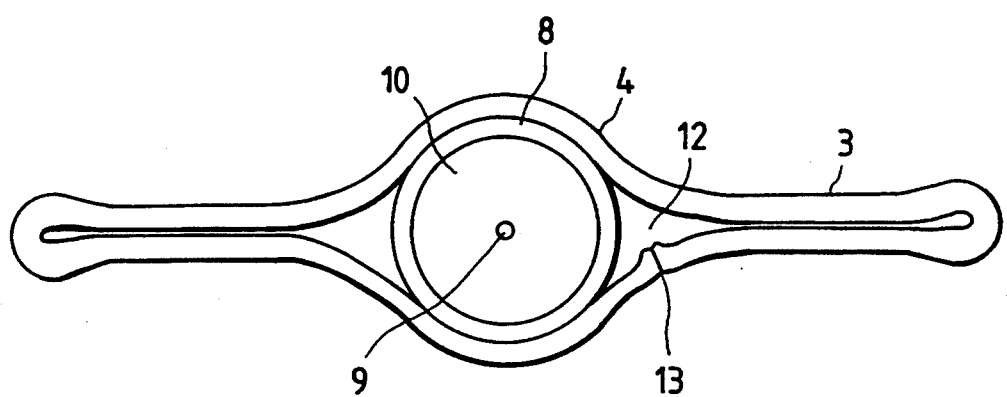
FIG. 4 is a sectional view of a fin arrangement and a heater in the deodorant equipment of FIG. 1.

The metal tube heater 2 is inserted into the aluminized steel tube 11. Then, the aluminized steel tube 11 is made into a fin arrangement 4 by a pressing and deforming process. Specifically, as shown in FIG. 4, diametrically-opposed regions of the aluminized steel tube 11 are pressed and made into rectangular flat radiators 3 by press dies. At the same time, portions of the aluminized steel tube 11 are pressed against and curved along the outer surfaces of the metal tube 8 of the heater 2. As a result, a base of the fin arrangement 4 is completed which securely fits on the metal tube 8 of the heater 2. The fin arrangement 4 is thus fixed to the metal tube heater 2.

During the process of making the fin arrangement 4, inner spaces 12 are formed between the walls of the fin arrangement 4 (the aluminized steel tube 11) and the walls of the metal tube 8 of the heater 2. The inner spaces 12 extend along the longitudinal direction (the axial direction) of the metal tube heater 2. The welded portion 13 of the fin arrangement 4 (the aluminized steel tube 11) is located at a position facing one of the inner spaces 12, so that the welded portion 13 is prevented from damaging the surfaces of the metal tube 8 of the heater 2.

After the fin arrangement 4 has been made, an inner layer 5a of a vitreous coating film 5 is formed on the outer surfaces of the fin arrangement 4 by an application process. The application of the material for the inner layer 5a to the outer surfaces of the fin arrangement 4 is executed by a suitable process such as a spraying process or a dipping process. An outer layer 5b of the vitreous coating film 5 is formed on the surfaces of the inner layer 5a by an application process and a firing process. The application of the material for the outer layer 5b to the outer surfaces of the inner layer 5a is executed by a suitable process such as a spraying process or a dipping process. The vitreous coating film 5 is thus completed. Protective layers 6 are formed on the ends of the fin arrangement 4 and the vitreous coating film 5 in the length direction (the longitudinal direction) of the fin arrangement 4 by an application process. Generally, it is difficult to form the vitreous coating film 5 on the ends of the fin arrangement 4 in the length direction (the longitudinal direction) thereof. Thus, the ends of the fin arrangement 4 tend to be uncovered from the vitreous coating film 5. The protective layers 6 cover the ends of the fin arrangement 4, and prevent the ends of the fin arrangement 4 from being corroded by a catalyst layer 7 which will be made later.

During a subsequent period, activated alumina, silica, zeolite, and others are adequately mixed by a ball mill into a mixture, from which slurry is adjusted. The slurry is applied to an exposed region of the outer surfaces of the vitreous coating film 5. The applied slurry is fired to form a porous absorption layer 7a on the vitreous coating film 5. The application of the slurry to the outer surfaces of the vitreous coating film 5 is executed by a suitable process such as a spraying process or a dipping process. A platinum solution and a palladium (platinum group metal) solution are applied to the outer surfaces of the absorption layer 7a. The platinum solution and the palladium solution are made by dissolving platinum and palladium in, for example, nitric acid solutions. The applied platinum solution and palladium solution are fired to form a metal catalyst layer 7b which has metal (platinum and palladium) carried on the outer surfaces of the porous absorption layer 7a. Thus, the metal catalyst layer 7b is also made porous. The application of the platinum solution and the palladium solution to the outer surfaces of the absorption layer 7a is executed by a suitable process such as a spraying process or a dipping process. The absorption layer 7a and the metal catalyst layer 7b compose a catalyst layer 7 of a two-layer structure.

At a final stage of the manufacture of the deodorant equipment 1, ends of the metal tube 8 of the heater 2 are sealed by glass sealant 14.

Figure 5:
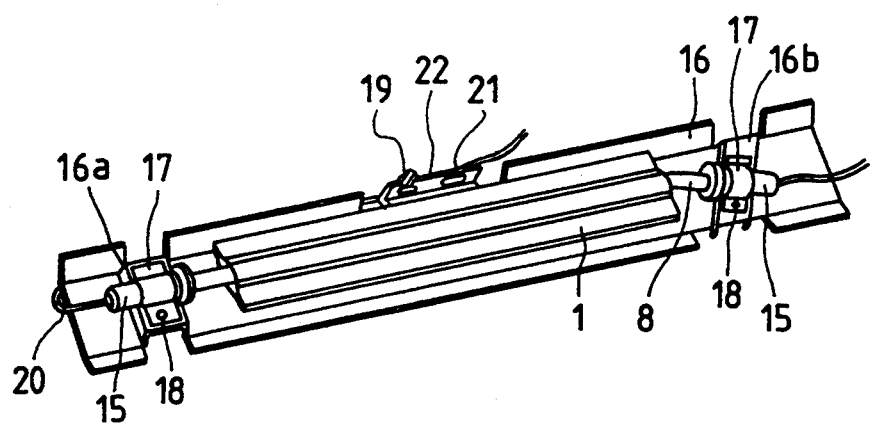
FIG. 5 is a perspective view of the deodorant equipment of FIG. 1 and parts attached thereto.

Parts attached to the deodorant equipment 1 will now be described with reference to FIG. 5. Insulating caps 15 are provided on ends of the metal tube 8 of the heater 2 respectively. The caps 15 are made of suitable insulating material such as silicone rubber. A heat insulating plate 16 is attached to the deodorant equipment 1 by suitable members in a manner such that the heat insulating plate 16 separates from the catalyst layer 7 of the fin arrangement 4 of the deodorant equipment 1 by a predetermined space. The heat insulating plate 16 is made of, for example, steel. The heat insulating plate 16 serves to block the transmission of heat. Attachment members 17 have a cross section of a shape of a character "Ω". The insulating caps 15 extend through circular portions of the attachment members 17. The insulating caps 15 are retained by the attachment members 17. Flat portions of the attachment members 17 are fixed to projections 16a and 16b of the heat insulating plate 16 by screws 18. In this way, the heat insulating plate 16 is attached to the deodorant equipment 1. The projections 16a and 16b separate the heat insulating plate 16 from the fin arrangement 4 by a predetermined space.

One end of the metal tube 8 of the heater 2 which is uncovered from the fin arrangement 4 is bent by an angle of, for example, 30°. After the heat insulating plate 16 is attached to the deodorant equipment 1, the bent configuration of the metal tube 8 prevents rotation of the deodorant equipment 1 about the metal tube 8 which would change the relative positional relation between the fin arrangement 4 and the heat insulating plate 16 from a normal positional relation and thus which might cause the heat insulating plate 16 to be excessively heated.

One end of a bimetallic thermo-device or thermostat 19 is electrically connected to an end of the electric resistance wire 9 by leads 20. The other end of the bimetallic thermo-device 19 is electrically connected to one end of a thermal fuse 21 by leads 22. In this way, the electric resistance wire 9, the bimetallic thermo-device 19, and the thermal fuse 21 are connected in series. The bimetallic thermo-device 19 and the thermal fuse 21 are mounted on the heat insulating plate 16 by, for example, screws.

The bimetallic thermo-device 19 operates to detect that the deodorant equipment 1 is excessively heated. If such an overheating condition occurs, the bimetallic thermo-device 19 changes from an on state to an off state to interrupt the supply of a drive current to the electric resistance wire 9 of the heater 2. Thus, the temperature of the catalyst layer 7 of the deodorant equipment 1 is prevented from rising into an unacceptable high range so that the characteristics of the catalyst layer 7 are prevented from deteriorating. If the bimetallic thermo-device 19 fails to respond to the previously-mentioned overheating condition, the thermal fuse 21 is blown off to interrupt the supply of a drive current to the electric resistance wire 9 of the heater 2.

Figure 6:
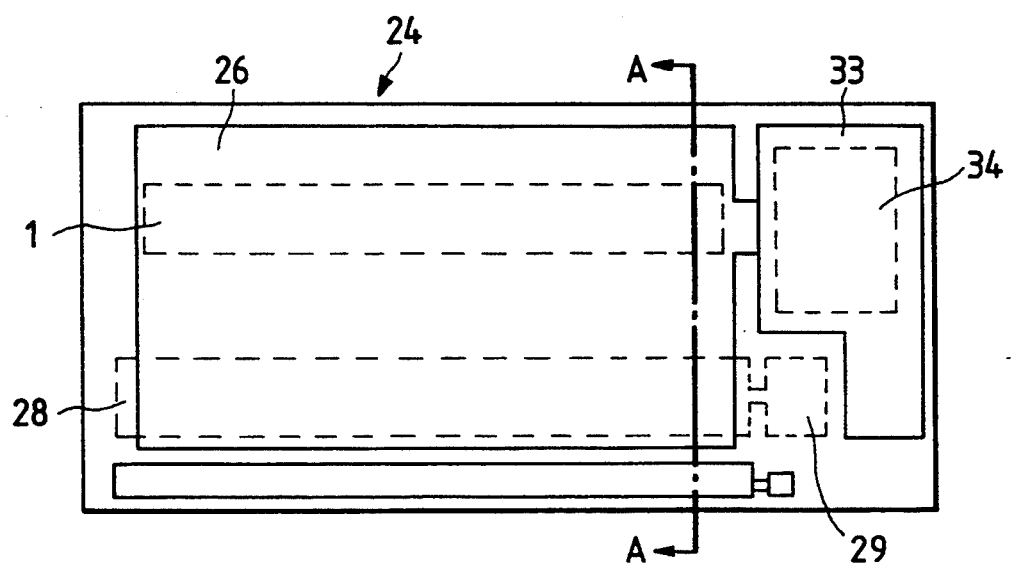
FIG. 6 is a diagram of an indoor unit of an air conditioner which contains the deodorant equipment of FIG. 1.
Figure 7:
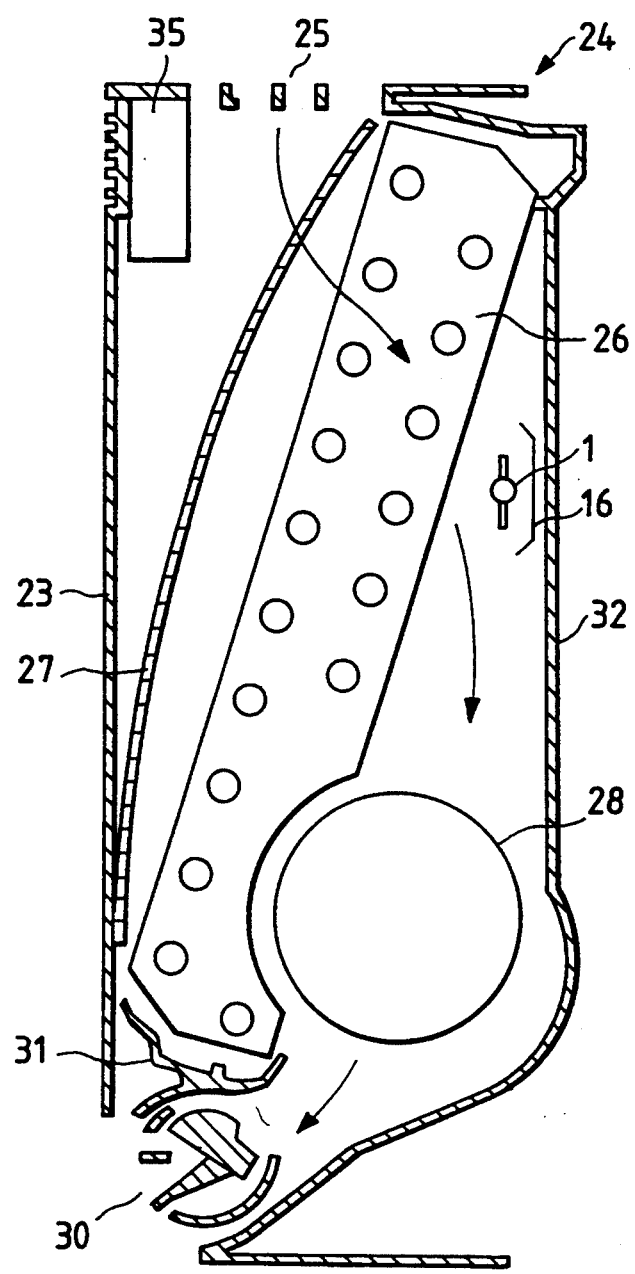
FIG. 7 is a sectional view of the indoor unit taken along the line A—A in FIG. 6.

An air conditioner has a combination of an outdoor unit and a wall-mounted indoor unit 24 which is shown in FIGS. 6 and 7. The indoor unit 24 includes a housing which has a front panel 23. An upper portion of the housing of the indoor unit 24 is formed with an inlet 25 for the introduction of air into the housing. A heat exchanger 26 is disposed in the indoor unit 24. The heat exchanger 26 serves to cool or heat air. A filter 27 disposed in the indoor unit 24 removes dust from air which flows from the air inlet 25 to the heat exchanger 26.

A fan or blower 28 disposed in the indoor unit 24 draws air into the indoor unit 24 via the air inlet 25, and then drives the air through the filter 27 and the heat exchanger 26 and expels the air from the indoor unit 24 via an air outlet 30. The fan 28 is located in a portion of the air flow path downstream of the heat exchanger 26. The air outlet 30 is provided in a lower portion of the housing of the indoor unit 24. The fan 28 is activated by a drive motor 29 disposed in the indoor unit 24. A drain pan 31 disposed in the indoor unit 24 extends below a lower end of the heat exchanger 26. The drain pan 31 receives water drained from the heat exchanger 26, and then transmits the water toward a drain pipe (not shown).

The combination of the deodorant equipment 1 and the heat insulating plate 16 is disposed in the indoor unit 24. The combination of the deodorant equipment 1 and the heat insulating plate 16 is mounted on a rear panel 32 of the housing of the indoor unit 24 by screws or others. The deodorant equipment 1 is located in a portion of the air flow path between the heat exchanger 26 and the fan 28. The radiators 3 of the deodorant equipment 1 are oriented along the direction of the air flow. The heat insulating plate 16 is placed between the deodorant equipment 1 and the rear panel 32 of the housing of the indoor unit 24.

An electric box 33 disposed in the indoor unit 24 includes a control circuit 34 which operates and controls the deodorant equipment 1. The control circuit 34 also controls the air conditioner, and determines a mode of operation of the air conditioner from among a cooling mode, a heating mode, an air blowing mode, and a dehumidifying mode. Accordingly, the control circuit 34 knows the current mode of operation of the air conditioner. An odor sensor 35 is fixedly disposed in an upper portion of the indoor unit 24 near the air inlet 25. The odor sensor 35 detects an odor or odors of air introduced into the indoor unit 24 via the air inlet 25.

Figure 24:
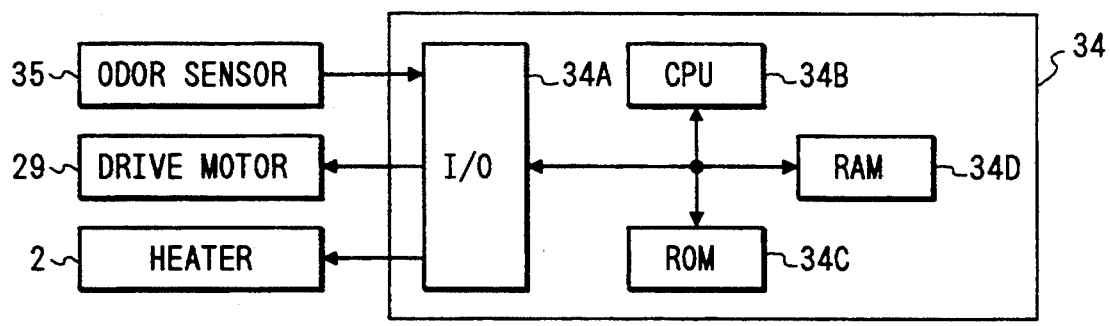
FIG. 24 is a block diagram of the combination of the odor sensor, the control circuit, the fan drive motor, and the heater in the indoor unit of FIG. 6.

As shown in FIG. 24, the control circuit 34 is electrically connected to the electric resistance wire 9 of the heater 2, the fan drive motor 29, and the odor sensor 35. The control circuit 34 operates to control the electric resistance wire 9 and the fan drive motor 29 in response to an output signal of the odor sensor 35 which represents the detected odor of air. The control circuit 34 includes a microcomputer or a similar device having a combination of an I/O port 34A, a CPU 34B, a ROM 34C, and a RAM 34D. The electric resistance wire 9 of the heater 2, the fan drive motor 29, and the odor sensor 35 are electrically connected to the I/O port 34A. The control circuit 34 operates in accordance with a program stored in the ROM 34C.

Figure 8:
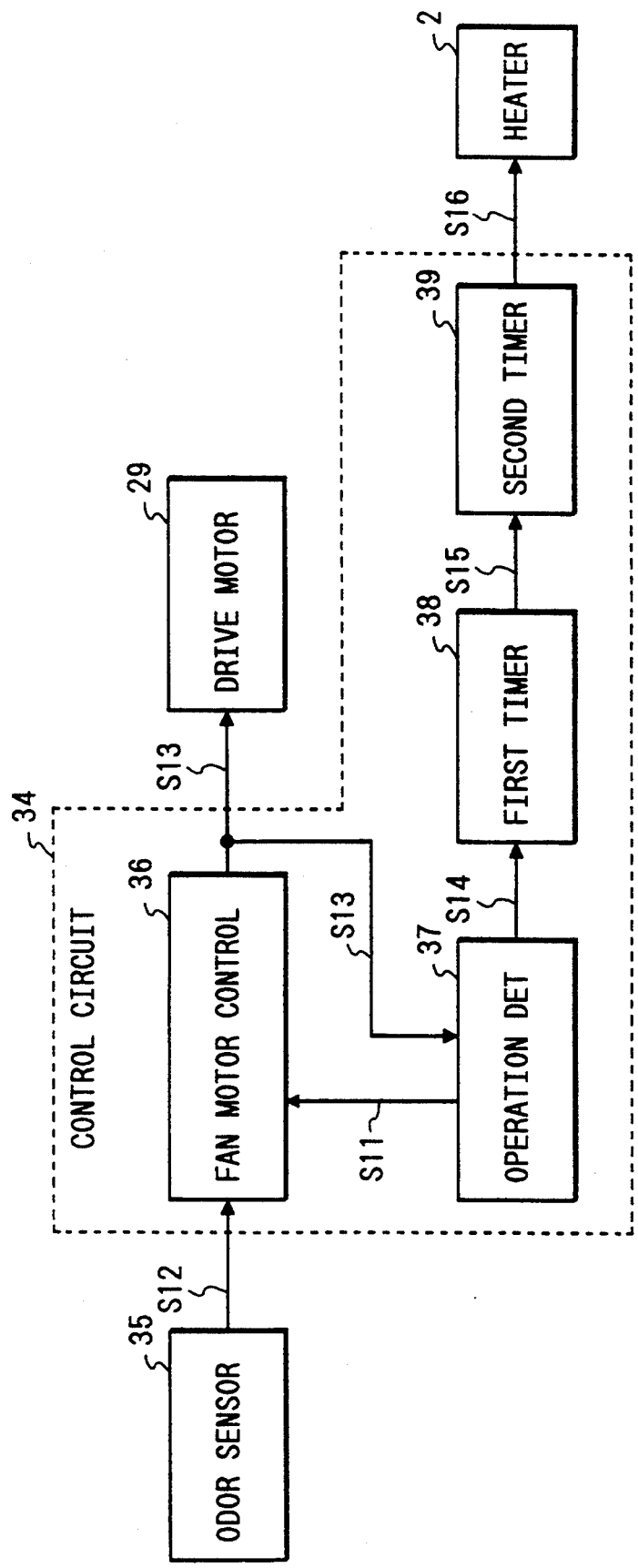
FIG. 8 is a diagram of a combination of an odor sensor, a control circuit, a fan drive motor, and a heater in the indoor unit of FIG. 6.

FIG. 8 is a diagram of the function of the control circuit 34. In FIG. 8, under conditions where an operation detecting section 37 feeds a fan motor control section 36 with a signal S11 representing that the indoor unit 24 is being suspended, the fan motor control section 36 outputs a signal S13 to the fan drive motor 29 to activate the latter when the fan motor control section 36 receives a signal S12 from the odor sensor 35 which represents the presence of an odor of air. The operation detecting section 37 serves to detect whether the indoor unit 24 is being activated or suspended by referring to the output signal S13 of the fan motor control section 36. When the indoor unit 24 is being activated, the operation detecting section 37 outputs a signal S14 to a first timer 38. The first timer 38 measures the total period "ta" for which the indoor unit 24 is activated by referring to the output signal S14 of the operation detecting section 37. When the measured total period "ta" reaches a given time "Ta", the first timer 38 resets the measured total period "ta" to zero and outputs a signal S15 to a second timer 39. Upon the reception of the output signal S15 of the first timer 38, the second timer 39 feeds the metal tube heater 2 with a signal S16 which energizes the metal tube heater 2. The second timer 39 holds the metal tuber heater 2 energized by a given time "Tb". Specifically, the second timer 39 measures the period "tb" for which the metal tube heater 2 remains energized. When the period "tb" measured by the second timer 39 reaches the given time "Tb", the second timer 39 de-energizes the metal tube heater 2. The first and second timers 38 and 39 are provided by either a software or a hardware.

Figure 9:
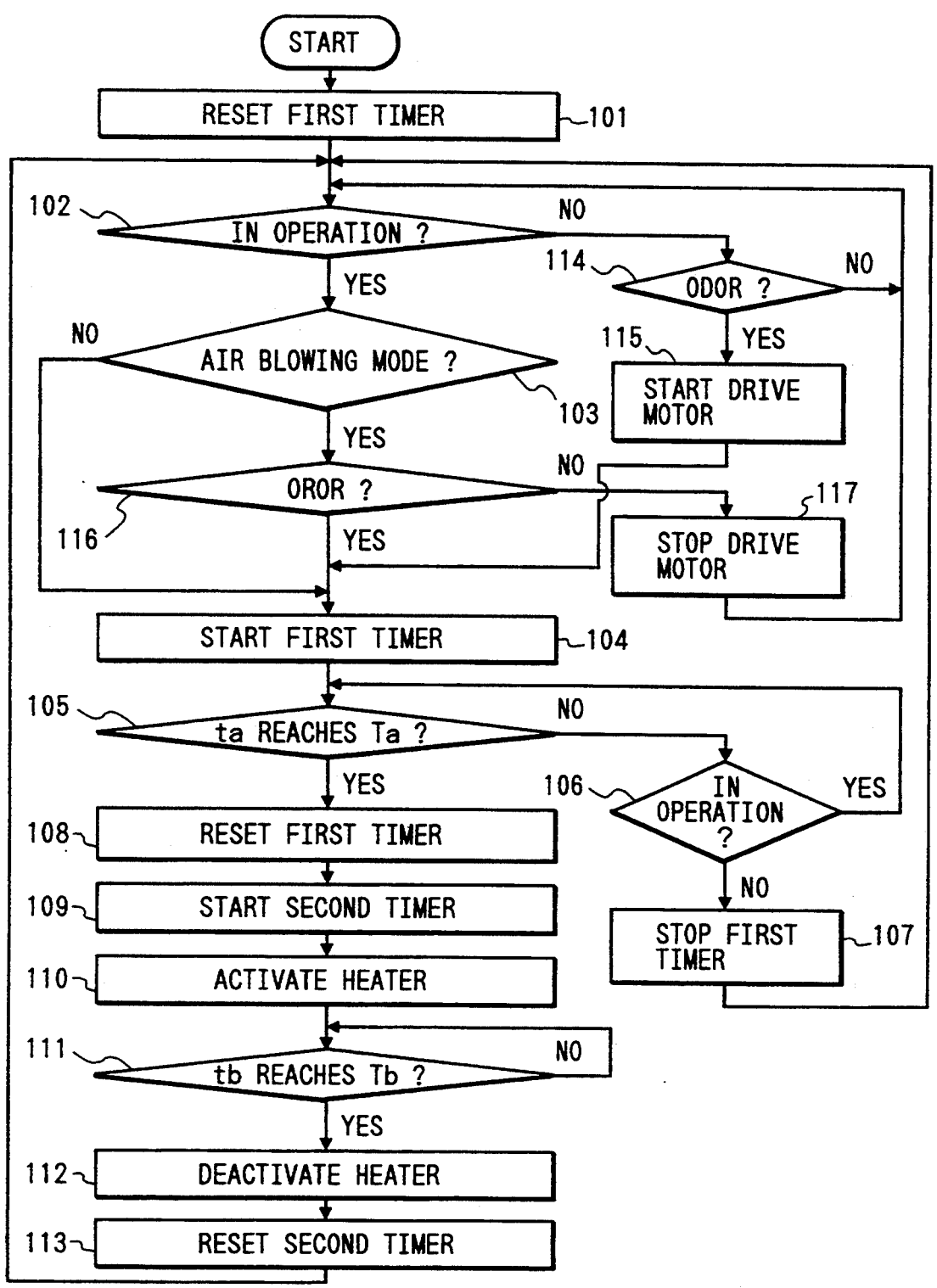
FIG. 9 is a flowchart of a segment of a program for operating the control circuit in the indoor unit of FIG. 6.

As previously described, the control circuit 34 operates in accordance with a program stored in the ROM 34C. FIG. 9 is a flowchart of a segment of the program which is designed to control the metal tube heater 2 and the fan drive motor 29. The segment of the program is started when a main power supply switch of the air conditioner is moved to an on position.

As shown in 9, a first step 101 of the segment of the program resets the period "ta" measured by the first timer 38. After the step 101, the program advances to a step 102.

The step 102 detects whether the indoor unit 24 is being activated or suspended. When the indoor unit 24 is detected to be being activated, the program advances to a step 103. Otherwise, the program advances to a step 114.

The step 103 detects whether or not a mode of operation of the indoor unit 24 agrees with an air blowing mode. When the mode of operation of the indoor unit 24 is detected to be equal to the air blowing mode, the program advances to a step 116. Otherwise, the program advances to a step 104 which starts the first timer 38.

The step 114 decides whether or not an odor of air is present by referring to the output signal of the odor sensor 35. When an odor of air is decided to be present, the program advances to a step 115 which activates the fan drive motor 29. Otherwise, the program returns to the step 102. After the step 115, the program advances to the step 104 which stats the first timer 104.

The step 116 decides whether or not an odor of air is present by referring to the output signal of the odor sensor 35. When an odor of air is decided to be present, the program advances to the step 104 which starts the first timer 38. Otherwise, the program advances to a step 117 which stops the fan drive motor 29. After the step 117, the program returns to the step 102.

The step 105 decides whether or not the time "ta" measured by the first timer 38 reaches the given time "Ta". When the time "ta" measured by the first timer 38 reaches the given time "Ta", the program advances to a step 108. Otherwise, the program advances to a step 106.

The step 106 detects whether the indoor unit 24 is being activated or suspended. When the indoor unit 24 is detected to be being activated, the program returns to the step 105. Otherwise, the program advances to a step 107 which stops the first timer 38. After the step 107, the program returns to the step 102.

The step 108 resets the period "ta" measured by the first timer 38. A step 109 following the step 108 starts the second timer 109. A step 110 following the step 109 energizes the metal tube heater 2. After the step 110, the program advances to a step 111.

The step 111 decides whether or not the time "tb" measured by the second timer 39 reaches the given time "Tb". When the time "tb" measured by the second timer 39 reaches the given time "Tb", the program advances to a step 112. Otherwise, the step 111 repeated.

The step 112 de-energizes the metal tube heater 2. A step 113 following the step 112 resets the period "tb" measured by the second timer 39. After the step 113, the program returns to the step 102.

The operation of the air conditioner will be further described. When the main power supply switch of the air conditioner is moved to the on position, the period "ta" measured by the first timer 38 is reset (the step 101). When the indoor unit 24 of the air conditioner is operated in a cooling mode, a heating mode, or a dehumidifying mode (the step 102 and 103), the first timer 38 is started (the step 104). During the operation of the indoor unit 24, the fan 28 enables air to be drawn into the indoor unit 24 via the air inlet 25, and the air is then driven through the filter 27 and the heat exchanger 26 and is emitted from the indoor unit 24 via the air outlet 30.

When the air is driven through the indoor unit 24, the air encounters the catalyst layer 7 of the deodorant equipment 1 so that odor components of the air are absorbed by activated alumina and zeolite in the absorption layer 7a of the catalyst layer 7. Thus, the air is deodorized. Activated alumina forms a carrier which provides a porous structure of the absorption layer 7a. Basic material is carried on the carrier so that acid substances are absorbed by the absorption layer 7a. On the other hand, zeolite mainly absorbs basic substances.

During an interval until the period "ta" measured by the first timer 38 reaches the given period "Ta", as long as the indoor unit 24 remains operated, the steps 105 and 106 are reiterated. When the indoor unit 24 is suspended, the first timer 38 is stopped (the step 107). Then, the step 102 is executed again.

When the period "ta" measured by the first timer 38 reaches the given period "Ta", the measured period "ta" is reset (the step 108) and the second timer 39 is started {the step 109). In addition, the metal tube heater 2 Is energized (the step 110).

As a result, the electric resistance wire 9 of the metal tube heater 2 is heated so that the metal tube 8 and the fin arrangement 4 are also heated. This heating process activates platinum group metal in the metal catalyst layer 7b of the catalyst layer 7, and also separates the odor components from activated alumina and zeolite in the absorption layer 7. Activated platinum group metal exhibits an effective catalytic function which oxidizes and decomposes the odor components into odorless substances. Accordingly, the odor components are removed from activated alumina and zeolite so that odor-absorbing abilities of activated alumina and zeolite are recovered. In addition, the odor components are converted into odorless substances.

When the period "tb" measured by the second timer 39 reaches the given period "Tb", the metal tube heater 2 is de-energized (the step 112). In addition, the the period "tb" measured by the second timer 39 is reset (the step 113). Then, the step 102 is executed again.

In the case where the step 102 decides the indoor unit 24 to be being suspended, when the output signal of the odor sensor 35 indicates the presence of an odor of air (the step 114), the fan drive motor 29 is activated (the step 115) so that the air blowing mode of operation of the indoor unit 24 is performed. On the other hand, when the output signal of the odor sensor 35 indicates the absence of an odor of air (the step 114), the step 102 is executed again.

In the case where the step 103 decides the mode of operation of the indoor unit 24 to be equal to the air blowing mode, when the output signal of the odor sensor 35 indicates the presence of an odor of air (the step 116), the first timer 38 is started (the step 104). On the other hand, when the output signal of the odor sensor 35 indicates the absence of an odor of air (the step 116), the fan drive motor 29 is stopped (the step 117) to suspend the air blowing mode of operation of the indoor unit 24. Then, the step 102 is executed again.

As previously described, the vitreous coating film 5 covers at least a part of outer surfaces of the fin arrangement 4 through which the metal tube heater 2 extends. The catalyst layer 7 formed on the vitreous coating film 5 contains at least activated alumina, silica, zeolite, and platinum group metal. While the metal tube heater 2 remains de-energized, activated alumina mainly absorbs stinking acid substances and zeolite mainly absorbs stinking basic substances. Thus, a stinking-substance absorbing process is executed. When the metal tube heater 2 is energized, the stinking substances are separated from activated alumina and zeolite and are decomposed by the catalytic function of platinum group metal in the catalyst layer 7 so that odor-absorbing abilities of activated alumina and zeolite are recovered. Thus, an absorbing-ability recovering process is executed. The stinking-substance absorbing process and the absorbing-ability recovering process are cyclically and periodically reiterated so that stinking substances can be removed from air for a long time.

As previously described, the catalyst layer 7 has a laminate of the inner layer and the outer layer, that is, the absorption layer 7a and the metal catalyst layer 7b. This configuration of the catalyst layer 7 ensures that, when the metal tube heater 2 is energized, odor components of air adjoining the catalyst layer 7 are efficiently oxidized and decomposed into odorless substances. In addition, since the odor components separated from activated alumina and zeolite always pass through the metal catalyst layer 7b, it is possible to reliably prevent the odor components from being returned to air without being decomposed into odorless substances. Furthermore, since the total amount of expensive platinum group metal is generally smaller than that in a reference design having a catalyst layer of a single-layer configuration, the cost of manufacture of the deodorant equipment 1 can be suppressed.

The catalyst layer 7 uses silica as an inorganic binder. Therefore, a bonding force of the carrier for activated alumina is increased so that an adequate stiffness of the catalyst layer 7 is attained without decreasing a catalyst activity.

As previously described, the vitreous coating film 5 has a laminate of the inner layer and the outer layer, that is, the dense-texture layer 5a and the coarse-texture layer 5b. The dense-texture layer 5a reduces the number of pin holes in the vitreous coating film 5 so that the surfaces of the fin arrangement 4 is reliably prevented from being corroded by the catalyst layer 7. The coarse-texture layer 5b provides good characteristics of bonding between the vitreous coating film 5 and the catalyst layer 7.

The fin arrangement 4 includes a tubular base which covers the metal tube heater 2. The fin arrangement 4 also includes radiators 3 projecting outward from the tubular base thereof. The catalyst layer 7 is provided on the outer surfaces of the fin arrangement 4 including the projecting radiators 3, so that a large total area of the outer surfaces of the catalyst layer 7 is attained without increasing the size of the metal tube heater 2.

The metal tube heater 2 withstands a shock. In addition, the electrically-insulating and thermally-conducting material 10 and the metal tube 8 efficiently transmit heat from the electric resistance wire 9 to the fin arrangement 4.

As previously described, the fin arrangement 4 is made of aluminized steel. In general, aluminized steel exhibits a small thermal expansion at high temperatures. Thus, when the fin arrangement 4 is heated by the metal tube heater 2, a resultant thermal expansion of the fin arrangement 4 is small so that the vitreous coating film 5 and the catalyst layer 7 are reliably prevented from being broken and cracked thereby.

The protective layers 6 are formed on the ends of the fin arrangement 4 and the vitreous coating film 5 in the length direction (the longitudinal direction) of the fin arrangement 4. It is difficult to form the vitreous coating film 5 on the ends of the fin arrangement 4 in the length direction (the longitudinal direction) thereof. Thus, the ends of the fin arrangement 4 tend to be uncovered from the vitreous coating film 5. The protective layers 6 cover the ends of the fin arrangement 4, and prevent the ends of the fin arrangement 4 from being corroded by the catalyst layer 7.

The fin arrangement 4 is made of aluminized steel. It is easy to fix the aluminized-steel fin arrangement 4 to the metal tube 8 of the heater 2. Also, it is easy to form the aluminized-steel fin arrangement 4 with the radiators 3. Since the inner surfaces of the fin arrangement 4 and the outer surfaces of the metal tube heater 2 can be held in close contact with each other, it is possible to efficiently transmit heat from the metal tube heater 2 to the fin arrangement 4.

As previously described, the radiators 3 of the fin arrangement 4 are oriented along the direction of the air flow in the indoor unit 24. This orientation of the radiators 3 is advantageous in suppressing an increase in a resistance to the air flow. In addition, the orientation provides a long time during which air and the catalyst layer 7 remain in contact with each other, so that a large percentage of odor components of air can be absorbed by the catalyst layer 7.

In the case where the indoor unit 24 of the air conditioner is being suspended, when the odor sensor 35 detects the presence of an odor of air, the air blowing mode of operation of the indoor unit 24 is started and the metal tube heater 2 is periodically energized so that deodorization of air is automatically executed.

DESCRIPTION OF THE SECOND PREFERRED EMBODIMENT

Figure 10:
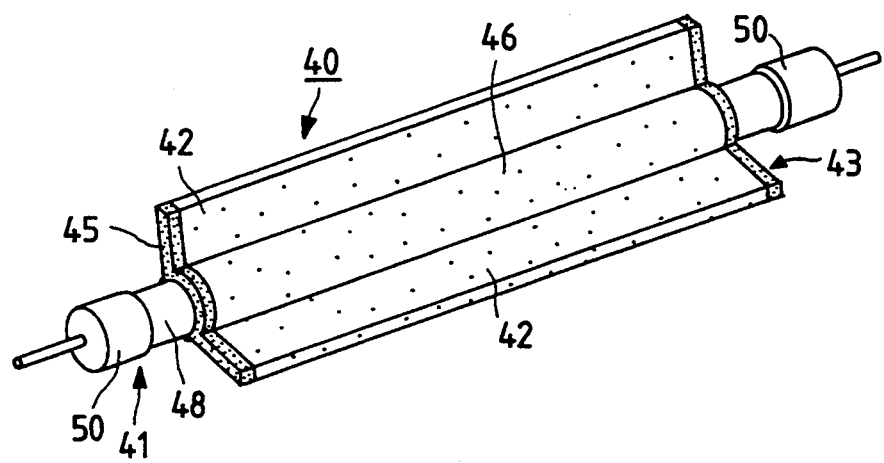
FIG. 10 is a perspective view of a deodorant equipment according to a second embodiment of this invention.
Figure 11:
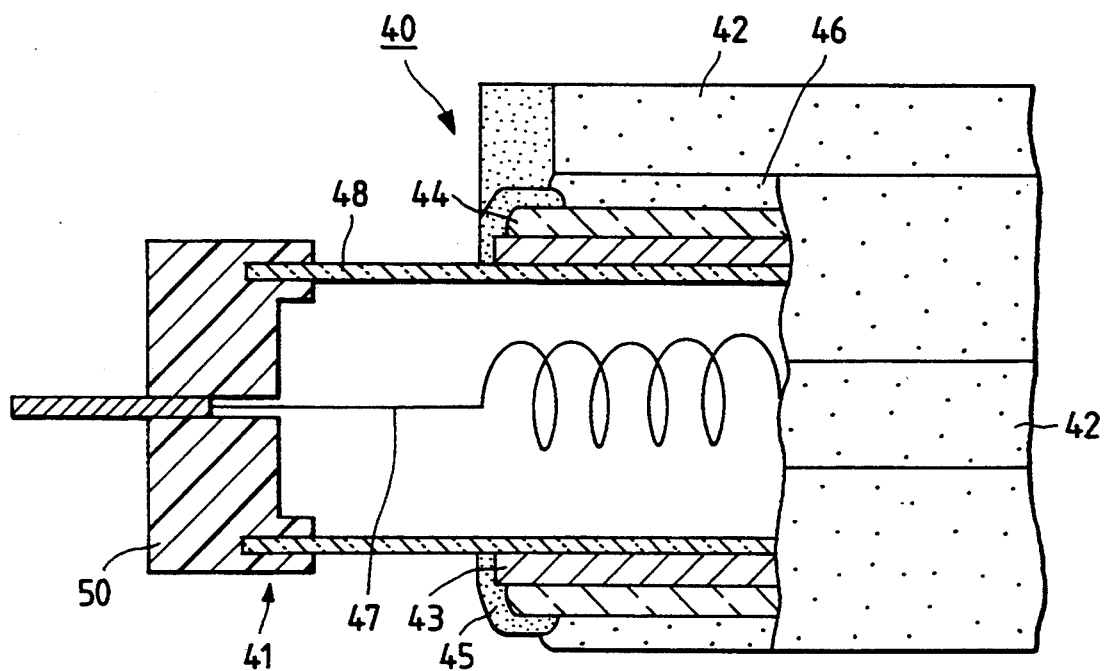
FIG. 11 is a side view, partially in cross section, of the deodorant equipment of FIG. 10.

With reference to FIGS. 10 and 11, a deodorant equipment 40 includes a glass tube heater 41, a fin arrangement 43, a vitreous coating film 44, protective layers 45, and a catalyst layer 46.

The glass tube heater 41 includes a glass tube 48 and an electric resistance wire (a heating wire) 47. The electric resistance wire 47 extends through the interior of the glass tube 48. The electric resistance wire 47 is separated from and supported on the glass tube 48 by insulating caps 50 provided on ends of the glass tube 48.

The fin arrangement 43 is made of aluminized steel. The fin arrangement 43 includes a tubular base, and radiators 42 projecting outward from the tubular base. The base of the fin arrangement 43 entirely or partially covers an effective heating region of surfaces of the glass tube heater 41. The radiators 42 of the fin arrangement 43 are integral with the base of the fin arrangement 43. The radiators 42 are spaced by an angle smaller than 180°. The radiators 42 have a rectangular flat configuration. The radiators 42 extend along the longitudinal direction (the axial direction) of the glass tube heater 41.

The vitreous coating film 44 covers at least a part of outer surfaces of the fin arrangement 43. The vitreous coating film 44 is made of glass material or similar material. The protective layers 45 are made of a heat-resisting and rust-preventing paint. The protective layers 45 cover respective ends of the fin arrangement 43 in the length direction (the longitudinal direction) thereof. The protective layers 45 also cover ends of the vitreous coating film 44.

The catalyst layer 46 is formed on the vitreous coating film 44. The catalyst layer 46 contains at least activated alumina, silica, and platinum group metal. The catalyst layer 46 is porous.

The deodorant equipment 40 is manufactured as follows. First, an electric resistance wire or a heating wire 47 is inserted into a glass tube 48. Then, insulating caps 50 are attached to ends of the glass tube 48 to fabricate a glass tube heater 41. The electric resistance wire 47 extends through the insulating caps 50.

Figure 12:
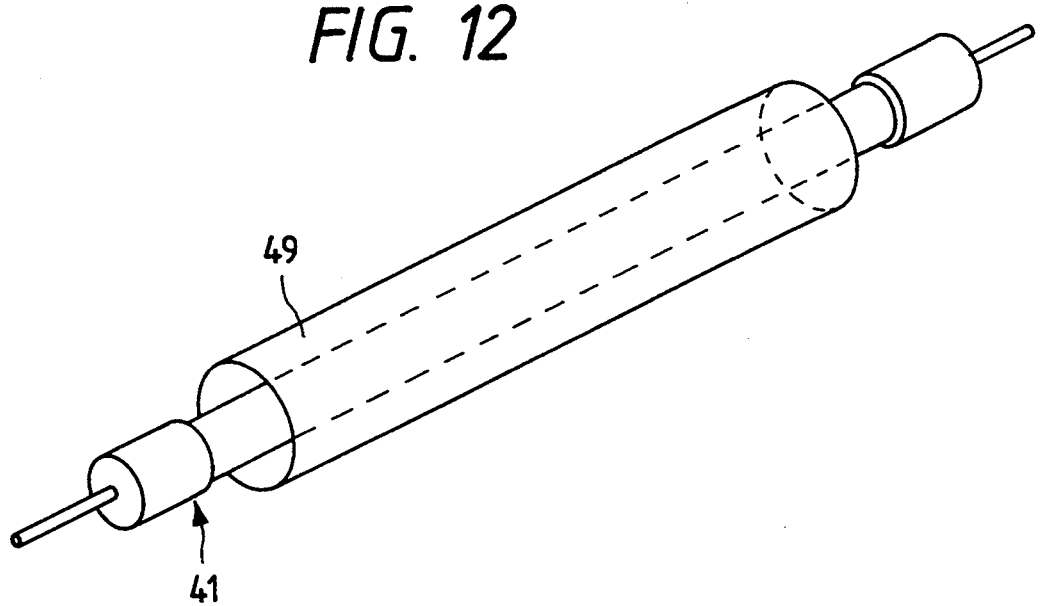
FIG. 12 is a perspective view of a heater and a metal tube used for a fin arrangement in the deodorant equipment of FIG. 10.

During a subsequent period, as shown in FIG. 12, the glass tube heater 41 is inserted into an aluminized steel tube 49. Then, the aluminized steel tube 49 is made into a fin arrangement 43 by a pressing and deforming process. Specifically, regions of the aluminized steel tube 49 which are separated by an angle smaller than 180° are pressed and made into rectangular flat radiators 42 by press dies. At the same time, portions of the aluminized steel tube 49 are pressed against and curved along the outer surfaces of the glass tube 48 of the heater 41. As a result, a base of the fin arrangement 43 is completed which securely fits on the glass tube 48 of the heater 41. The fin arrangement 43 is thus fixed to the glass tube heater 41.

After the fin arrangement 43 has been made, a vitreous coating film 44 is formed on the outer surfaces of the fin arrangement 43 by an application process and a firing process. The application of the material for the vitreous coating film 44 to the outer surfaces of the fin arrangement 43 is executed by a suitable process such as a spraying process or a dipping process. Protective layers 45 made of a heat-resisting and rust-preventing paint are formed on the ends of the fin arrangement 43 and the vitreous coating film 44 in the length direction (the longitudinal direction) of the fin arrangement 43 by an application process. Generally, it is difficult to form the vitreous coating film 44 on the ends of the fin arrangement 43 in the length direction (the longitudinal direction) thereof. Thus, the ends of the fin arrangement 43 tend to be uncovered from the vitreous coating film 44. The protective layers 45 cover the ends of the fin arrangement 43, and prevent the ends of the fin arrangement 43 from being corroded by a catalyst layer 46 which will be made later.

During a subsequent period, activated alumina, silica, platinum, palladium, and others are adequately mixed by a ball mill into a mixture, from which slurry is adjusted. The slurry is applied to an exposed region of the outer surfaces of the vitreous coating film 44. The applied slurry is fired to form a porous catalyst layer 46 on the vitreous coating film 44. The application of the slurry to the outer surfaces of the vitreous coating film 44 is executed by a suitable process such as a spraying process or a dipping process.

Figure 13:
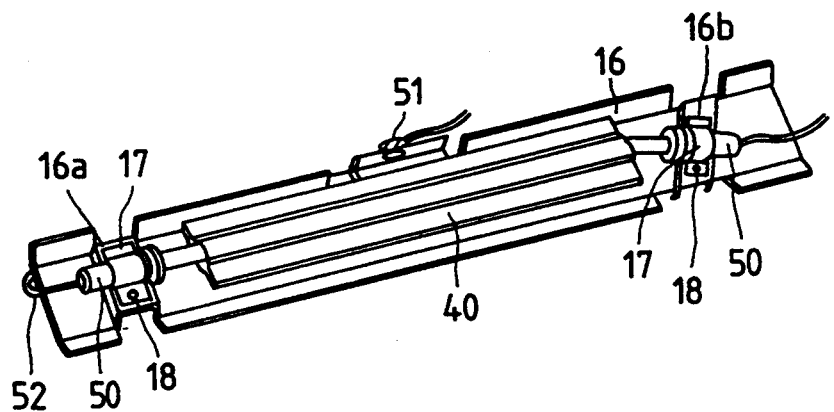
FIG. 13 is a perspective view of the deodorant equipment of FIG. 10 and parts attached thereto.

Parts attached to the deodorant equipment 40 will now be described with reference to FIG. 13. Insulating caps 50 are provided on ends of the glass tube 48 of the heater 41 respectively. The caps 50 are made of suitable insulating material such as silicone rubber. A heat insulating plate 16 is attached to the deodorant equipment 40 by suitable members in a manner such that the heat insulating plate 16 separates from the catalyst layer 46 of the fin arrangement 43 of the deodorant equipment 40 by a predetermined space. The heat insulating plate 16 is made of, for example, steel. The heat insulating plate 16 serves to block the transmission of heat. Attachment members 17 have a cross section of a shape of a character "Ω". The insulating caps 50 extend through circular portions of the attachment members 17. The insulating caps 50 are retained by the attachment members 17. Flat portions of the attachment members 17 are fixed to projections 16a and 16b of the heat insulating plate 16 by screws 18. In this way, the heat insulating plate 16 is attached to the deodorant equipment 40. The projections 16a and 16b separate the heat insulating plate 40 from the fin arrangement 43 by a predetermined space.

One end of the glass tube 48 of the heater 41 which is uncovered from the fin arrangement 43 is bent by an angle of, for example, 30°. After the heat insulating plate 16 is attached to the deodorant equipment 40, the bent configuration of the glass tube 48 prevents rotation of the deodorant equipment 40 about the glass tube 48 which would change the relative positional relation between the fin arrangement 43 and the heat insulating plate 16 from a normal positional relation, and thus which might cause the heat insulating plate 16 to be excessively heated.

One end of a bimetallic thermo-device or thermostat 51 is electrically connected to an end of the electric resistance wire 47 by leads 52. Thus, the electric resistance wire 47 and the bimetallic thermo-device 51 are connected in series. The bimetallic thermo-device 51 is mounted on the heat insulating plate 16 by, for example, screws.

The bimetallic thermo-device 51 operates to detect that the deodorant equipment 40 is excessively heated. If such an overheating condition occurs, the bimetallic thermo-device 51 changes from an on state to an off state to interrupt the supply of a drive current to the electric resistance wire 47 of the heater 41. Thus, the temperature of the catalyst layer 46 of the deodorant equipment 40 is prevented from rising into an unacceptable high range so that the characteristics of the catalyst layer 46 are prevented from deteriorating.

Figure 14:
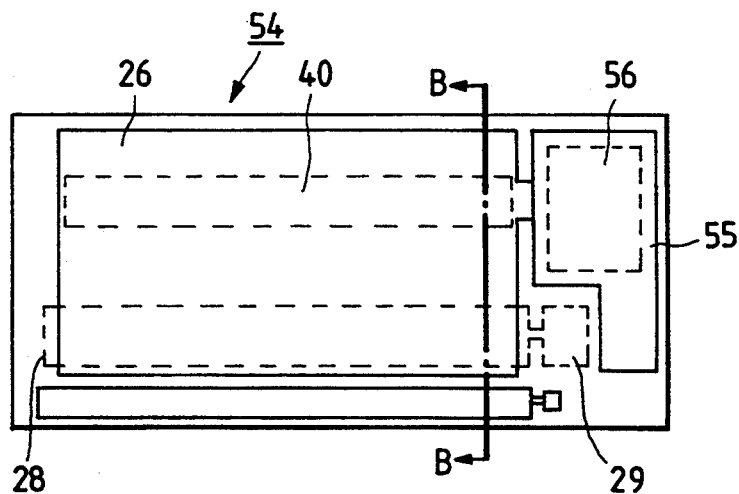
FIG. 14 is a diagram of an indoor unit of an air conditioner which contains the deodorant equipment of FIG. 10.
Figure 15:
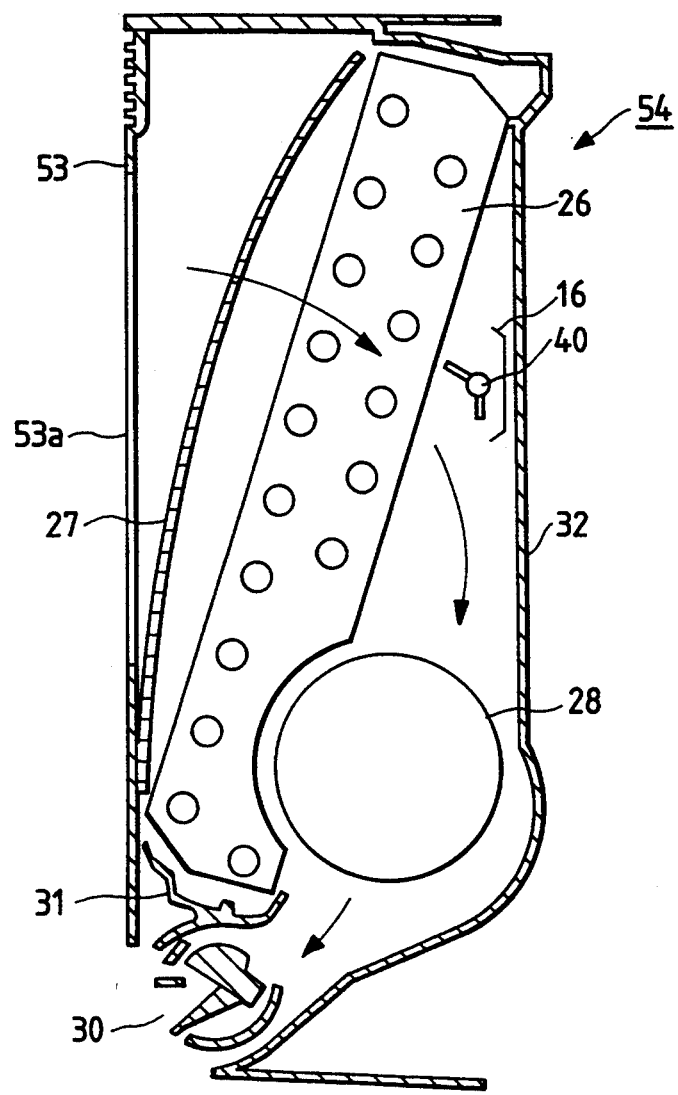
FIG. 15 is a sectional view of the indoor unit taken along the line B—B in FIG. 14.

An air conditioner has a combination of an outdoor unit and a wall-mounted indoor unit 54 which is shown in FIGS. 14 and 15. The indoor unit 54 includes a housing which has a front panel 53 formed with an air inlet 53a. A heat exchanger 26 is disposed in the indoor unit 54. The heat exchanger 26 senses to cool or heat air. A filter 27 disposed in the indoor unit 54 removes dust from air which flows from the air inlet 53a to the heat exchanger 26.

A fan or blower 28 disposed in the indoor unit 54 draws air into the indoor unit 54 via the air inlet 53a, and then drives the air through the filter 27 and the heat exchanger 26 and expels the air from the indoor unit 54 via an air outlet 30. The fan 28 is located in a portion of the air flow path downstream of the heat exchanger 26. The air outlet 30 is provided in a lower portion of the housing of the indoor unit 54. The fan 28 is activated by a drive motor 29 disposed in the indoor unit 54. A drain pan 31 disposed in the indoor unit 54 extends below a lower end of the heat exchanger 26. The drain pan 31 receives water drained from the heat exchanger 26, and then transmits water toward a drain pipe (not shown).

The combination of the deodorant equipment 40 and the heat insulating plate 16 is disposed in the indoor unit 54. The combination of the deodorant equipment 40 and the heat insulating plate 16 is mounted on a rear panel 32 of the housing of the indoor unit 54 by screws or others. The deodorant equipment 40 is located in a portion of the air flow path between the heat exchanger 26 and the fan 28. The radiators 42 of the deodorant equipment 40 are oriented along the direction of the air flow. Specifically, the upstream radiator 42 extends toward the air inlet 53a while the downstream radiator 42 extends toward the fan 28. The heat insulating plate 16 is placed between the deodorant equipment 40 and the rear panel 32 of the housing of the indoor unit 54.

An electric box 55 disposed in the indoor unit 54 includes a control circuit 56 which operates and controls the deodorant equipment 40. The control circuit 56 also controls the air conditioner including the fan drive motor 29, and determines a mode of operation of the air conditioner from among a cooling mode, a heating mode, an air blowing mode, and a dehumidifying mode. Accordingly, the control circuit 56 knows the current mode of operation of the air conditioner.

Figure 25:
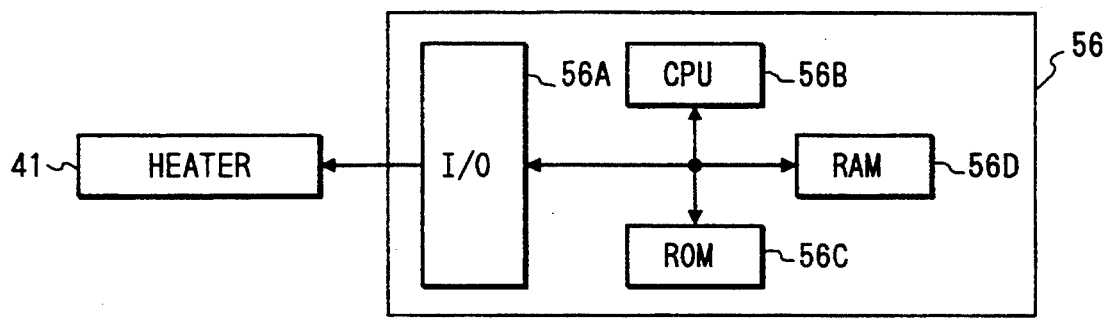
FIG. 25 is a block diagram of the combination of the control circuit and the heater in the indoor unit of FIG. 14.

As shown in FIG. 25, the control circuit 56 is electrically connected to the electric resistance wire 47 of the heater 41. The control circuit 56 operates to control the electric resistance wire 47. The control circuit 56 includes a microcomputer or a similar device having a combination of an I/0 port 56A, a CPU 56B, a ROM 56C, and a RAM 56D. The electric resistance wire 47 of the heater 41 is electrically connected to the I/O port 56A. The control circuit 56 operates in accordance with a program stored in the ROM 56C.

Figure 16:
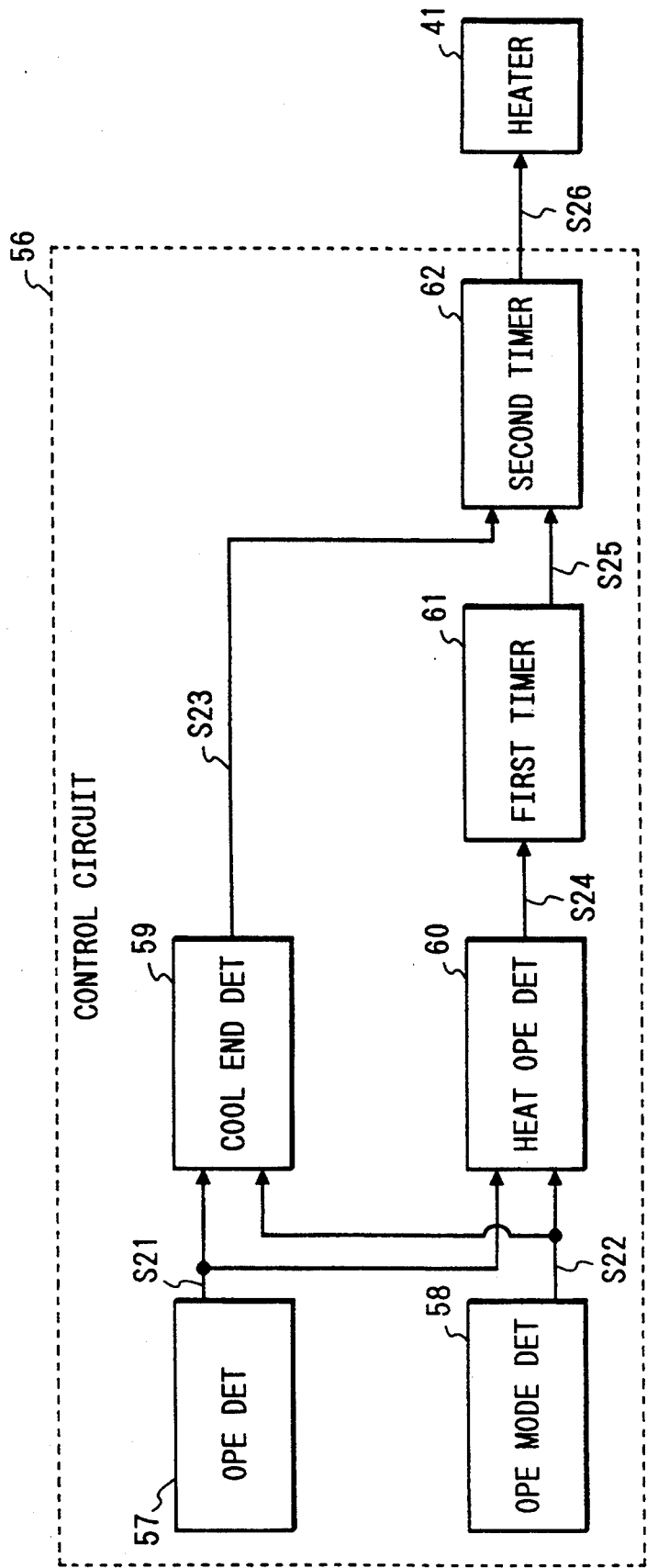
FIG. 16 is a diagram of a combination of a control circuit and a heater In the indoor unit of FIG. 14.

FIG. 16 is a diagram of the function of the control circuit 56. In FIG. 16, an operation detecting section 57 serves to detect whether the indoor unit 54 is being activated or suspended by referring to an output signal to the fan drive motor 29. The operation detecting section 57 outputs a signal S21 representing the result of the detection. An operation mode detecting section 58 serves to detect a mode of operation of the indoor unit 54. The operation mode detecting section 58 outputs a signal S22 representing the detected mode of operation of the indoor unit 54. A cooling mode end detecting section 59 serves to detect an end of a cooling mode of operation of the indoor unit 54 in response to the output signals S21 and S22 of the operation detecting section 57 and the operation mode detecting section 58. The cooling mode end detecting section 59 outputs a signal S23 representing the result of the detection. A heating mode detecting section 60 serves to detect whether or not the operation of the indoor unit 54 is currently in a heating mode by referring to the output signals S21 and S22 of the operation detecting section 57 and the operation mode detecting section 58. The heating mode detecting section 60 outputs a signal S24 representing the result of the detection. During the heating mode of operation of the indoor unit 54, a first timer 61 performs a time measuring process in response to the output signal S24 of the heating mode detecting section 60. Specifically, the first timer 61 measures the total period "ta" for which the indoor unit 54 is operated in the heating mode. When the measured total period "ta" reaches a given time "Ta", the first timer 61 resets the measured total period "ta" to zero and outputs a signal S25 to a second timer 62. Upon the reception of either the output signal S25 of the first timer 61 or the output signal S23 of the cooling mode end detecting section 59, the second timer 62 feeds the glass tube heater 41 with a signal S26 which energizes the glass tube heater 41. The second timer 62 holds the glass tube heater 41 energized by a given time "tb". Specifically, the second timer 62 measures the period "tb" for which the glass tube heater 41 remains energized. When the period "tb" measured by the second timer 62 reaches the given time "Tb", the second timer 62 de-energizes the glass tube heater 41. The first and second timers 61 and 62 are provided by either a software or a hardware.

Figure 17:
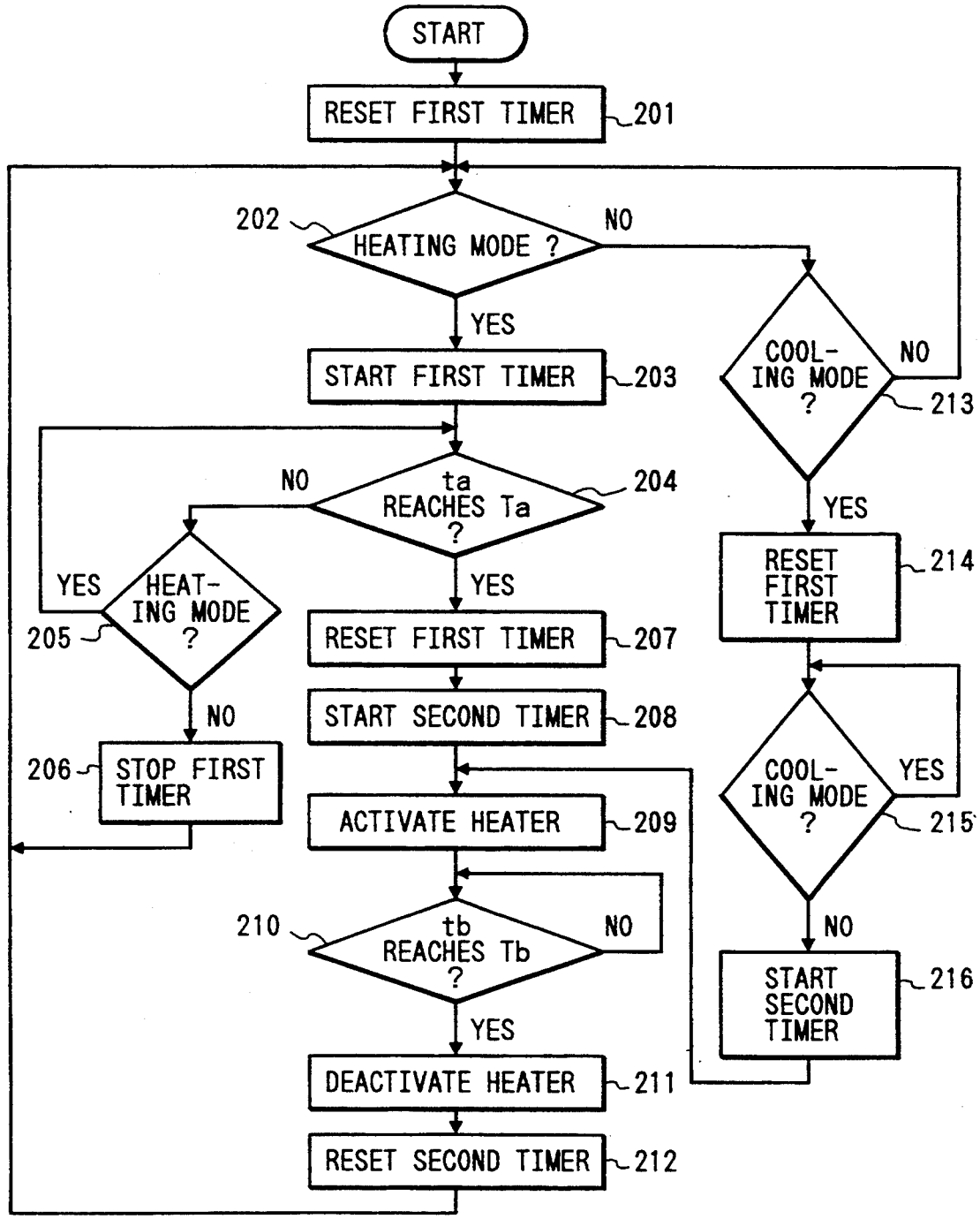
FIG. 17 is a flowchart of a segment of a program for operating the control circuit in the indoor unit of FIG. 14.

As previously described, the control circuit 56 operates in accordance with a program stored in the ROM 34C. FIG. 17 is a flowchart of a segment of the program which is designed to control the glass tube heater 41. The segment of the program is started when a main power supply switch of the air conditioner is moved to an on position.

As shown in 17, a first step 201 of the segment of the program resets the period "ta" measured by the first timer 61. After the step 201, the program advances to a step 202.

The step 202 detects whether or not the indoor unit 54 is operating in a heating mode. When the indoor unit 54 is detected to be operating in the heating mode, the program advances to a step 203. Otherwise, the program advances to a step 213.

The step 203 starts the first timer 61. After the step 203, the program advances to a step 204.

The step 204 decides whether or not the time "ta" measured by the first timer 61 reaches the given time "Ta". When the time "ta" measured by the first timer 61 reaches the given time "Ta", the program advances to a step 207. Otherwise, the program advances to a step 205.

The step 205 detects whether the indoor unit 54 is operating in the heating mode. When the indoor unit 54 is detected to be operating in the heating mode, the program returns to the step 204. Otherwise, the program advances to a step 206 which stops the first timer 61. After the step 206, the program returns to the step 202.

The step 207 resets the period "ta" measured by the first timer 61. A step 208 following the step 207 starts the second timer 62. After the step 208, the program advances to a step 209 which energizes the glass tube heater 41. After the step 209, the program advances to a step 210.

The step 210 decides whether or not the time "tb" measured by the second timer 62 reaches the given time "Tb". When the time "tb" measured by the second timer 62 reaches the given time "Tb", the program advances to a step 211. Otherwise, the step 210 repeated.

The step 211 de-energizes the glass tube heater 41. A step 212 following the step 211 resets the period "tb" measured by the second timer 62. After the step 212, the program returns to the step 202.

The step 213 detects whether or not the indoor unit 54 is operating in a cooling mode. When the indoor unit 54 is detected to be operating in the cooling mode, the program advances to a step 214. Otherwise, the program returns to the step 202.

The step 214 resets the period "ta" measured by the first timer 61. After the step 214, the program advances to a step 215.

The step 215 detects whether or not the indoor unit 54 is operating in the cooling mode. When the indoor unit 54 is detected to be operating in the cooling mode, the step 215 is repeated. Otherwise, the program advances to a step 216 which starts the second timer 62. Thus, when the cooling mode of operation of the indoor unit 54 terminates, the program proceeds from the step 215 to the step 216. After the step 216, the program advances to the step 209.

The operation of the air conditioner will be further described. When the main power supply switch of the air conditioner is moved to the on position, the period "ta" measured by the first timer 61 is reset (the step 201). When the indoor unit 54 of the air conditioner is operated in the heating mode (the step 202), the first timer 61 is started (the step 203). During the operation of the indoor unit 54, the fan 28 enables air to be drawn into the indoor unit 54 via the air inlet 53a, and the air is then driven through the filter 27 and the heat exchanger 26 and is emitted from the indoor unit 54 via the air outlet 30.

When the air is driven through the indoor unit 54, the air encounters the catalyst layer 46 of the deodorant equipment 40 so that odor components of the air are absorbed by activated alumina in the catalyst layer 46. Thus, the air is deodorized. Activated alumina forms a carrier which provides a porous structure of the catalyst layer 46. Basic material is carried on the carrier so that acid substances are absorbed by the catalyst layer 46.

During an interval until the period "ta" measured by the first timer 61 reaches the given period "Ta", as long as the indoor unit 54 remains operated in the heating mode, the steps 204 and 205 are reiterated. When the indoor unit 54 changes from the heating mode of operation, the first timer 61 is stopped (the step 206). Then, the step 202 is executed again.

When the period "ta" measured by the first timer 61 reaches the given period "Ta", the measured period "ta" is reset (the step 207) and the second timer 62 is started (the step 208). In addition, the glass tube heater 41 is energized (the step 209).

As a result, the electric resistance wire 47 of the glass tube heater 41 is heated so that the fin arrangement 43 is also heated. This heating process activates platinum group metal in the catalyst layer 46, and also separates the odor components from activated alumina in the catalyst layer 46. Activated platinum group metal exhibits an effective catalytic function which oxidizes and decomposes the odor components into odorless substances. Accordingly, the odor components are removed from activated alumina so that an odor-absorbing ability of activated alumina is recovered. In addition, the odor components are converted into odorless substances.

When the period "tb" measured by the second timer 62 reaches the given period "Tb", the glass tube heater 41 is de-energized (the step 211). In addition, the the period "tb" measured by the second timer 62 is reset (the step 212). Then, the step 202 is executed again.

In the case where the step 213 decides the indoor unit 54 to be operating in the cooling mode rather than the heating mode, the period "ta" measured by the first timer 61 is reset (the step 214). When the cooling mode of operation of the indoor unit 54 terminates (the step 215), the second timer 62 is started (the step 216). Then, the glass tube heater 41 is energized (the step 209).

As previously described, the vitreous coating film 44 covers at least a part of outer surfaces of the fin arrangement 43 through which the glass tube heater 41 extends. The catalyst layer 46 formed on the vitreous coating film 44 contains at least activated alumina, silica, and platinum group metal. While the glass tube heater 41 remains de-energized, activated alumina mainly absorbs stinking acid substances. Thus, a stinking-substance absorbing process is executed. When the glass tube heater 41 is energized, the stinking substances are separated from activated alumina and are decomposed by the catalytic function of platinum group metal in the catalyst layer 46 so that the odor-absorbing ability of activated alumina is recovered. Thus, an absorbing-ability recovering process is executed. The stinking-substance absorbing process and the absorbing-ability recovering process are cyclically and periodically reiterated so that stinking substances can be removed from air for a long time.

The catalyst layer 46 uses silica as an inorganic binder. Therefore, a bonding force of the carrier for activated alumina is increased so that an adequate stiffness of the catalyst layer 46 is attained without decreasing a catalyst activity.

The fin arrangement 43 includes a tubular base which covers the glass tube heater 41. The fin arrangement 43 also includes radiators 42 projecting outward from the tubular base thereof. The catalyst layer 46 is provided on the outer surfaces of the fin arrangement 43 including the projecting radiators 42, so that a large total area of the outer surfaces of the catalyst layer 46 is attained without increasing the size of the glass tube heater 41. The fin arrangement 43 protects the glass tube heater 41.

As previously described, the fin arrangement 43 is made of aluminized steel. In general, aluminized steel exhibits a small thermal expansion at high temperatures. Thus, when the fin arrangement 43 is heated by the glass tube heater 41, a resultant thermal expansion of the fin arrangement 43 is small so that the vitreous coating film 44 and the catalyst layer 46 are reliably prevented from being broken and cracked thereby.

The protective layers 45 are formed on the ends of the fin arrangement 43 and the vitreous coating film 44 in the length direction (the longitudinal direction) of the fin arrangement 43. It is difficult to form the vitreous coating film 44 on the ends of the fin arrangement 43 in the length direction (the longitudinal direction) thereof. Thus, the ends of the fin arrangement 43 tend to be uncovered from the vitreous coating film 44. The protective layers 45 covers the ends of the fin arrangement 43, and prevent the ends of the fin arrangement 43 from being corroded by the catalyst layer 46.

The fin arrangement 43 is made of aluminized steel. It is easy to fix the aluminized-steel fin arrangement 43 to the glass tube 48 of the heater 41. Also, it is easy to form the aluminized-steel fin arrangement 43 with the radiators 42. Since the inner surfaces of the fin arrangement 43 and the outer surfaces of the glass tube heater 41 can be held in close contact with each other, it is possible to efficiently transmit heat from the glass tube heater 41 to the fin arrangement 43.

As previously described, the radiators 42 of the fin arrangement 43 are oriented along the direction of the air flow in the indoor unit 54. This orientation of the radiators 42 is advantageous in suppressing an increase in a resistance to the air flow. In addition, the orientation provides a long time during which air and the catalyst layer 46 remain in contact with each other, so that a large percentage of odor components of air can be absorbed by the catalyst layer 46.

After the cooling mode of operation of the air conditioner terminates, the glass tube heater 41 is energized. Thus, energization of the glass tube heater 41 is unexecuted and discharge of hot air from the indoor unit 54 is prevented during the execution of the cooling mode of operation of the air conditioner.

DESCRIPTION OF THE THIRD PREFERRED EMBODIMENT

Figure 18:
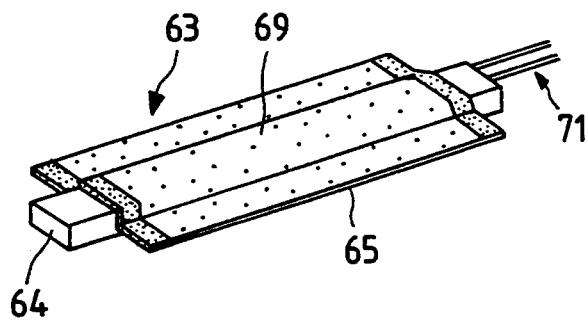
FIG. 18 is a perspective view of a deodorant equipment according to a third embodiment of this invention.
Figure 19:
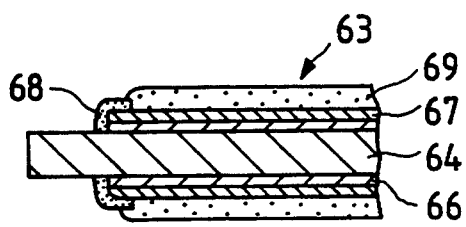
FIG. 19 is a sectional view of the deodorant equipment of FIG. 18.

With reference to FIGS. 18 and 19, a deodorant equipment 63 includes a ceramic heater 64, a fin arrangement 66, a vitreous coating film 67, protective layers 68, and a catalyst layer 69.

The ceramic heater 64 is of a bar configuration. The ceramic heater 64 includes an electric resistance wire or a heating wire surrounded by a ceramic block. The ceramic heater 64 is provided with a terminal 71 for connection with an external device.

The fin arrangement 66 is made of aluminum. The fin arrangement 66 includes an elongated rectangular base, and radiators 65 projecting outward from the rectangular base. The base of the fin arrangement 66 entirely or partially covers an effective heating region of surfaces of the ceramic heater 64. The radiators 65 of the fin arrangement 66 are integral with the base of the fin arrangement 66. The radiators 65 are spaced by an angle of 180°. The radiators 65 have a rectangular flat configuration. The radiators 65 extend along the longitudinal direction of the ceramic heater 64.

The vitreous coating film 67 covers at least a part of outer surfaces of the fin arrangement 66. The vitreous coating film 67 is made of glass material or similar material. The protective layers 68 are made of a heat-resisting and rust-preventing paint. The protective layers 68 cover respective ends of the fin arrangement 66 in the length direction (the longitudinal direction) thereof. The protective layers 68 also cover ends of the vitreous coating film 67.

The catalyst layer 69 is formed on the vitreous coating film 67. The catalyst layer 69 contains at least activated alumina, silica, and platinum group metal. The catalyst layer 69 is porous.

Figure 20:
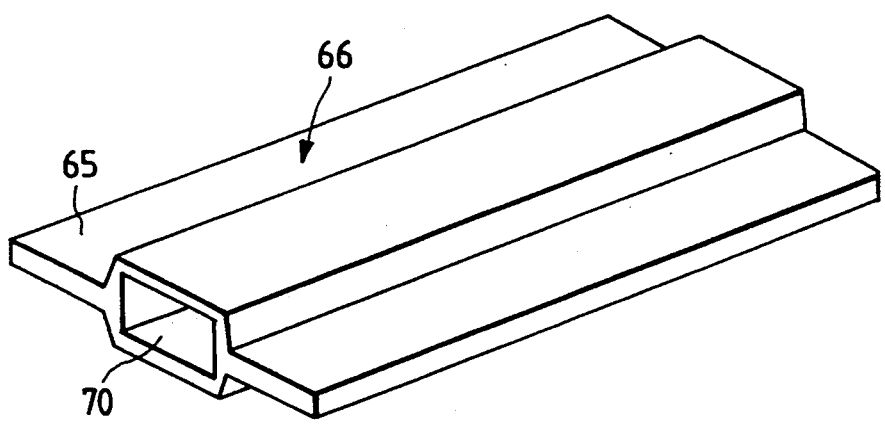
FIG. 20 is a perspective view of a fin arrangement in the deodorant equipment of FIG. 18.

The deodorant equipment 63 is manufactured as follows. First, a ceramic heater 64 is prepared. During a subsequent period, a fin arrangement 66 of aluminum is made by extrusion molding. As shown in FIG. 20, the fin arrangement 66 has an elongated rectangular base formed with a hole 70 for snugly accommodating the ceramic heater 64. The fin arrangement 66 has radiators 65 projecting from the base thereof.

Subsequently, a vitreous coating film 67 is formed on the outer surfaces of the fin arrangement 66 by an application process and a firing process. The application of the material for the vitreous coating film 67 to the outer surfaces of the fin arrangement 66 is executed by a suitable process such as a spraying process or a dipping process. Protective layers 68 made of a heat-resisting and rust-preventing paint are formed on the ends of the fin arrangement 66 and the vitreous coating film 67 in the length direction (the longitudinal direction) of the fin arrangement 66 by an application process. Generally, it is difficult to form the vitreous coating film 67 on the ends of the fin arrangement 66 in the length direction (the longitudinal direction) thereof. Thus, the ends of the fin arrangement 66 tend to be uncovered from the vitreous coating film 67. The protective layers 68 cover the ends of the fin arrangement 66, and prevent the ends of the fin arrangement 66 from being corroded by a catalyst layer 69 which will be made later.

During a subsequent period, activated alumina, silica, platinum, palladium, and others are adequately mixed by a ball mill into a mixture, from which slurry is adjusted. The slurry is applied to an exposed region of the outer surfaces of the vitreous coating film 67. The applied slurry is fired to form a porous catalyst layer 69 on the vitreous coating film 67. The application of the slurry to the outer surfaces of the vitreous coating film 67 is executed by a suitable process such as a spraying process or a dipping process.

Figure 21:
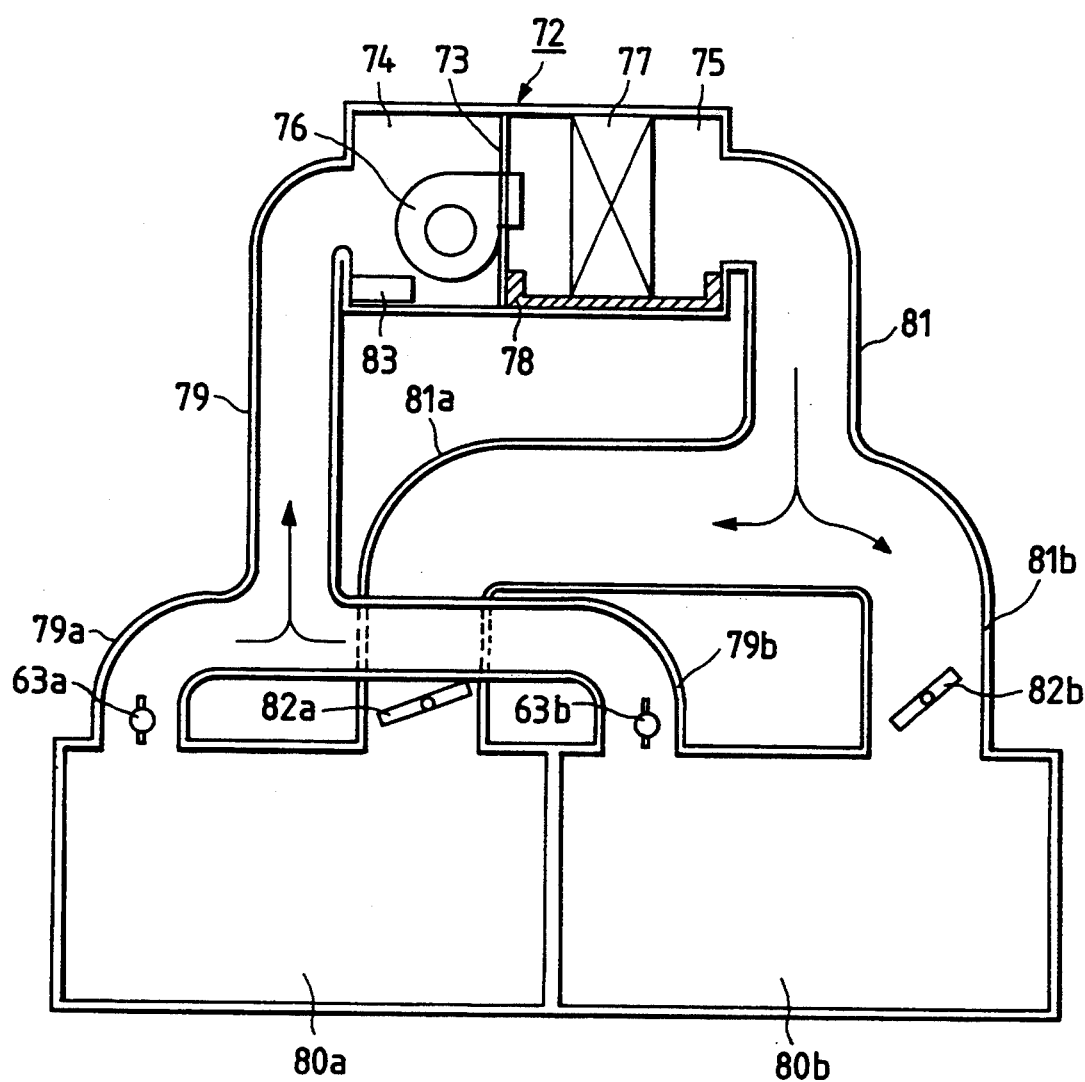
FIG. 21 is a diagram of an indoor unit of an air conditioner which contains the deodorant equipment of FIG. 18.

A duct-type air conditioner has a combination of an outdoor unit and an indoor unit 72 which is shown in FIG. 21. The indoor unit 72 has an interior which is divided by a partition wall 73 into an intake-side chamber 74 and a discharge-side chamber 75. A major part of a fan or blower 76 is disposed in the intake-side chamber 74. The fan 76 has an outlet projecting into the discharge-side chamber 75. The outlet of the fan 76 is open in the discharge-side chamber 75. A heat exchanger 77 is disposed in the discharge-side chamber 75. A drain pan 78 disposed in the discharge-side chamber 75 extends below the heat exchanger 77.

One end of an intake duct 79 communicates with the intake-side chamber 74. The other end of the intake duct 79 is forked into branches 79a and 79b which communicate with rooms 80a and 80b respectively. The rooms 80a and 80b are objects to be air-conditioned. One end of a discharge duct 81 communicates with the discharge-side chamber 75. The other end of the discharge duct 81 is forked into branches 81a and 81b which communicate with the rooms 80a and 80b respectively.

Movable dampers 82a and 82b disposed in the branches 81a and 81b of the discharge duct 81 serve to adjust the flow rates of air discharged into the rooms 80a and 80b from the indoor unit 72. The dampers 82a and 82b are controlled by an air flow rate controller (not shown).

Deodorant equipments 63a and 63b are disposed in the branches 79a and 79b of the intake duct 79 respectively. The deodorant equipments 63a and 63b are fixed to the walls of the intake duct 79 by suitable attachment devices (not shown). Each of the deodorant equipments 63a and 63b includes the deodorant equipment 63 of FIGS. 18 and 19.

An electric box 83 disposed in the indoor unit 72 includes a control circuit 91 which operates and controls the deodorant equipments 63a and 63b. The control circuit 91 also controls the air conditioner including a drive motor for the fan 76, and determines a mode of operation of the air conditioner from among a cooling mode, a heating mode, an air blowing mode, and a dehumidifying mode. Accordingly, the control circuit 91 knows the current mode of operation of the air conditioner.

Figure 26:
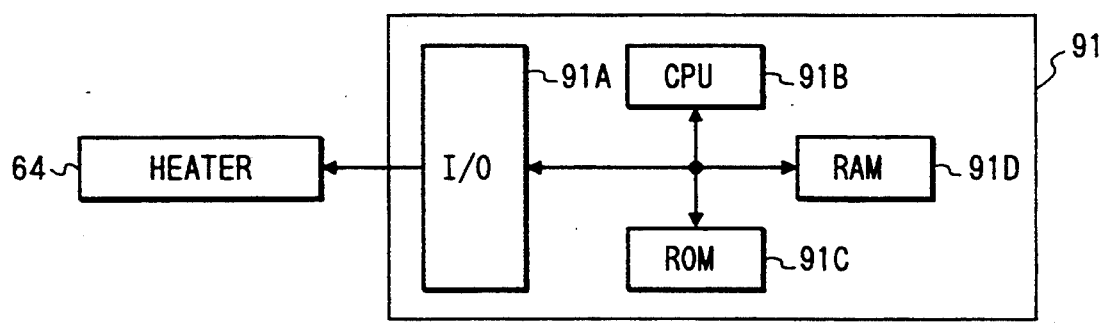
FIG. 26 is a block diagram of the combination of the control circuit and the heater in the indoor unit of FIG. 21.

As shown in FIG. 26, the control circuit 91 is electrically connected to the electric resistance wires of the ceramic heaters 64 in the deodorant equipments 63a and 63b. The control circuit 91 operates to control the ceramic heaters 64. The control circuit 91 includes a microcomputer or a similar device having a combination of an I/O port 91A, a CPU 91B, a ROM 91C, and a RAM 91D. The electric resistance wires of the ceramic heaters 64 are electrically connected to the I/O port 91A. The control circuit 91 operates in accordance with a program stored in the ROM 91C.

Figure 22:
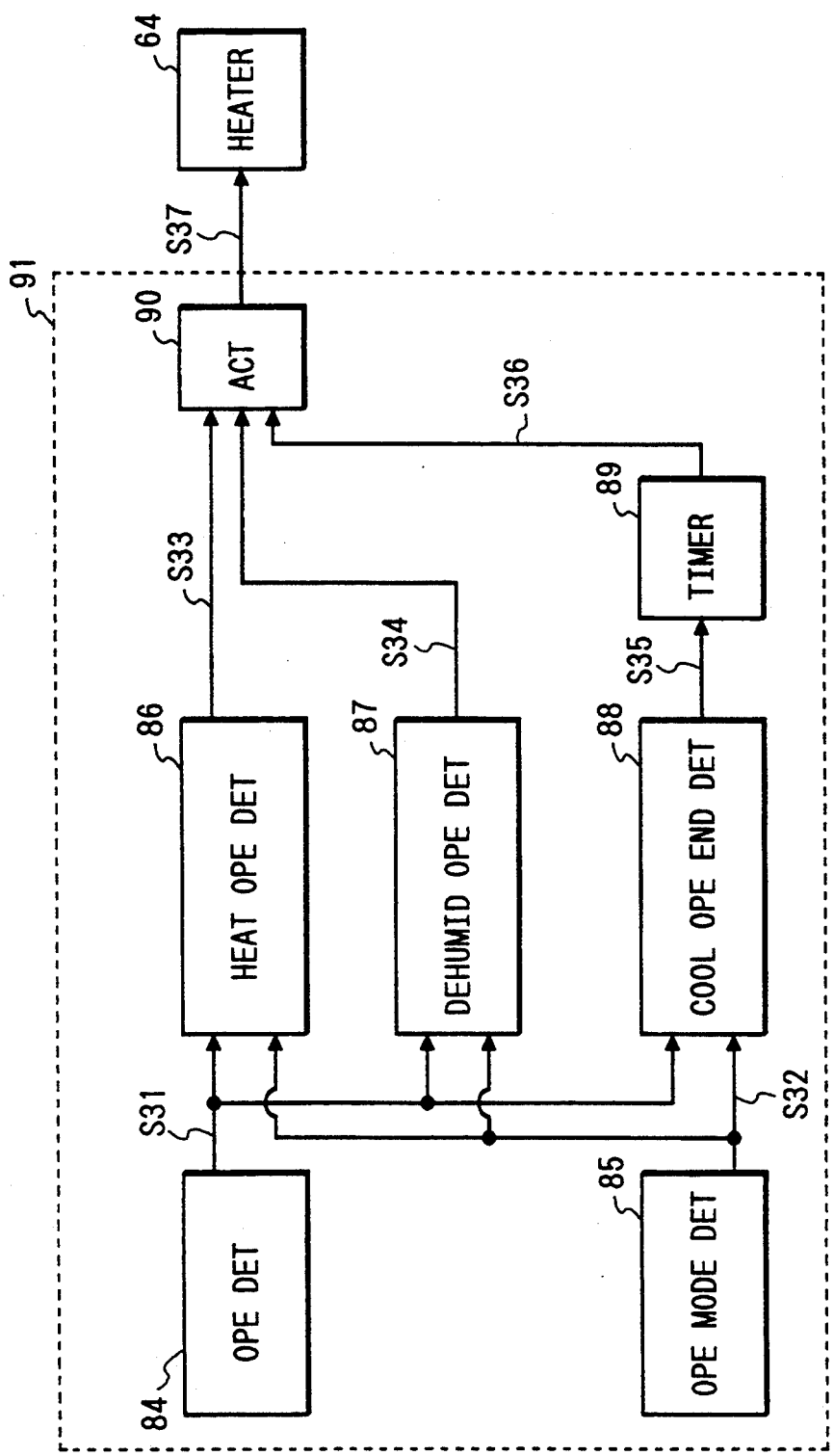
FIG. 22 is a diagram of a combination of a control circuit and a heater in the indoor unit of FIG. 21.

FIG. 22 is a diagram of the function of the control circuit 91. In FIG. 22, an operation detecting section 84 serves to detect whether the indoor unit 72 is being activated or suspended by referring to an output signal to the fan drive motor. The operation detecting section 84 outputs a signal S31 representing the result of the detection. An operation mode detecting section 85 serves to detect a mode of operation of the indoor unit 72. The operation mode detecting section 85 outputs a signal S32 representing the detected mode of operation of the indoor unit 72. A heating mode detecting section 86 serves to detect whether or not the indoor unit 72 is operating in a heating mode by referring to the output signals S31 and S32 of the operation detecting section 84 and the operation mode detecting section 85. While the indoor unit 72 is operating in the heating mode, the heating mode detecting section 86 continues to output a signal S33. A dehumidifying mode detecting section 87 serves to detect whether or not the indoor unit 72 is operating in a dehumidifying mode by referring to the output signals S31 and S32 of the operation detecting section 84 and the operation mode detecting section 85. While the indoor unit 72 is operating in the dehumidifying mode, the dehumidifying mode detecting section 87 continues to output a signal S34. A cooling mode end detecting section 88 serves to detect an end of a cooling mode of operation of the indoor unit 72 in response to the output signals S31 and S32 of the operation detecting section 84 and the operation mode detecting section 85. The cooling mode end detecting section 88 outputs a signal S35 representing the result of the detection. A timer 89 starts in response to the output signal S35 of the cooling mode end detecting section 88. During a given time "Tc" following the moment of the start of the timer 89, the timer 89 continues to output a signal S36. An energizing section 90 responds to the output signals S33, S34, and S36 of the heating mode detecting section 86, the dehumidifying mode detecting section 87, and the timer 89. When the energizing section 90 receives one of the signals S33, S34, and S36, the energizing section 90 outputs a signal S37 to the ceramic heaters 64 to energize them.

Figure 23:
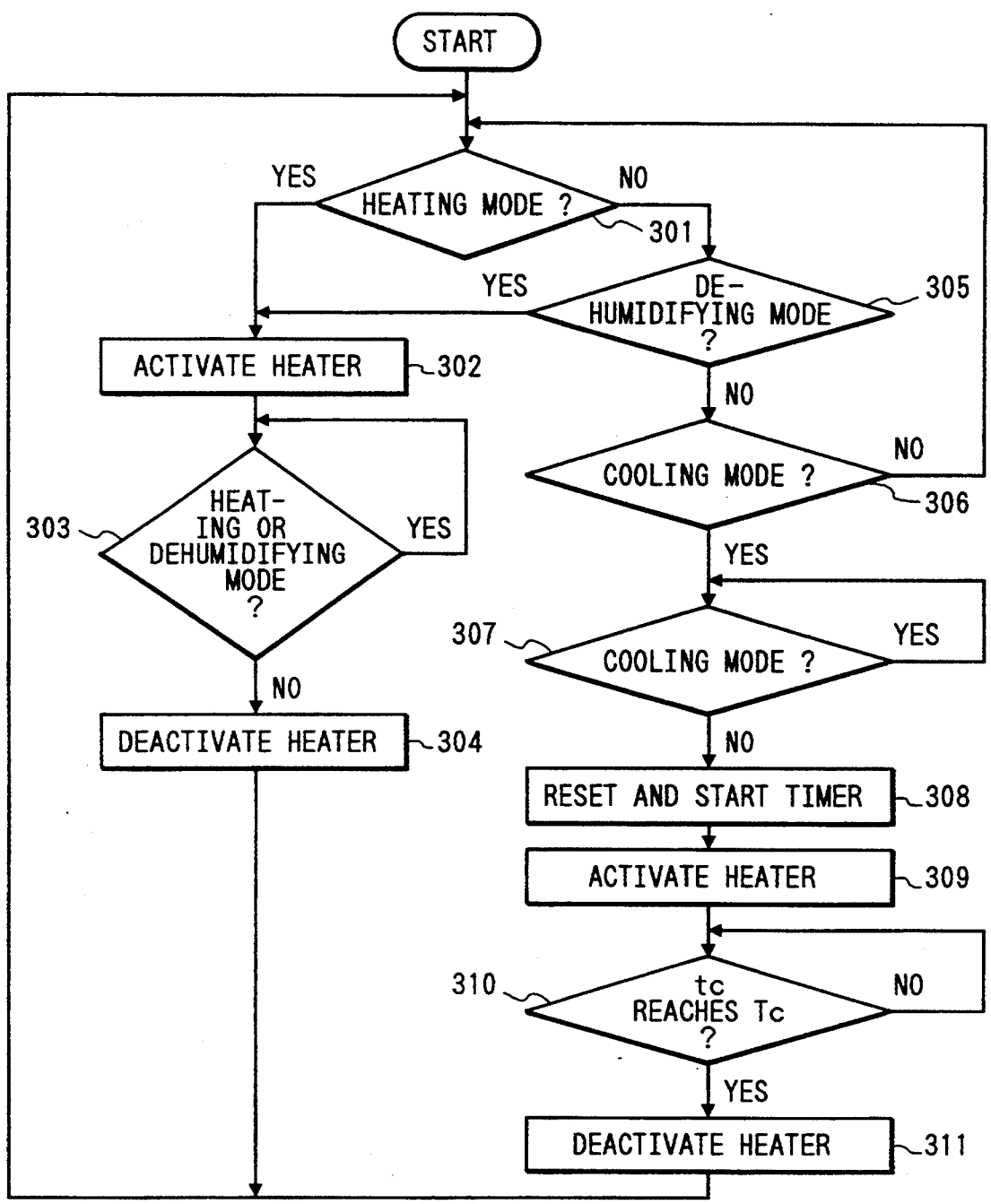
FIG. 23 is a flowchart of a segment of a program for operating the control circuit in the Indoor unit of FIG. 21.

As previously described, the control circuit 91 operates in accordance with a program stored in the ROM 91C. FIG. 23 is a flowchart of a segment of the program which is designed to control the ceramic heaters 64. The segment of the program is started when a main power supply switch of the air conditioner is moved to an on position.

As shown in 23, a first step 30 1 of the segment of the program detects whether or not the indoor unit 72 is operating in the heating mode. When the indoor unit 72 is detected to be operating in the heating mode, the program advances to a step 302. Otherwise, the program advances to a step 305.

The step 302 energizes the ceramic heaters 64. After the step 302, the program advances to a step 303.

The step 303 detects whether or not the indoor unit 72 is operating in one of the heating mode and the dehumidifying mode. When the indoor unit 72 is detected to be operating in one of the heating mode and the dehumidifying mode, the step 303 is repeated. When the indoor unit 72 is detected to be not operating in one of the heating mode and the dehumidifying mode, that is, when the heating mode or the dehumidifying mode of operation of the indoor unit 72 terminates, the program advances to a step 304.

The step 304 de-energizes the ceramic heaters 64. After the step 304, the program returns to the step 301.

The step 305 detects whether or not the indoor unit 72 is operating in the dehumidifying mode. When the indoor unit 72 is detected to be operating in the dehumidifying mode, the program advances to the step 302. Otherwise, the program advances to a step 306.

The step 306 detects whether or not the indoor unit 72 is operating in the cooling mode. When the indoor unit 72 is detected to be operating in the cooling mode, the program advances to a step 307. Otherwise, the program returns to the step 301.

The step 307 detects whether or not the indoor unit 72 is operating in the cooling mode. When the indoor unit 72 is detected to be operating in the cooling mode, the step 307 is repeated. When the indoor unit 72 is detected to be not operating in the cooling mode, that is, when the cooling mode of operation of the indoor unit 72 terminates, the program advances to a step 308.

The step 308 resets a period "tc" measured by the timer 89, and starts the timer 89. As a result, the timer 89 commences a time measuring process. A step 309 following the step 308 energizes the ceramic heaters 64. After the step 309, the program advances to a step 310.

The step 310 decides whether or not the time "tc" measured by the timer 89 reaches the given time "Tc". When the time "tc" measured by the timer 89 reaches the given time "Tc", the program advances to a step 311. Otherwise, the step 310 is repeated.

The step 311 de-energizes the ceramic heaters 64. After the step 311, the program returns to the step 301.

The operation of the air conditioner will be further described. During the operation of the indoor unit 72, the fan 76 enables air to be drawn into the indoor unit 72 from the rooms 80a and 80b via the branches 79a and 79b of the intake duct 79. The air is then guided along the intake duct 79, being successively driven through the fan 76 and the heat exchanger 77. The air undergoes a heat exchanging process in the heat exchanger 77. Subsequently, the air is moved along the discharge duct 81 and the branches 81a and 81b thereof before being discharged into the rooms 80a and 80b. The flow rates of air discharged into the rooms 80a and 80b are determined by the dampers 82a and 82b respectively.

When the main power supply switch of the air conditioner is moved to the on position and then the indoor unit 72 of the air conditioner is operated in the heating mode (the step 301), the ceramic heaters 64 in the deodorant equipments 63a and 63b are energized (the step 302).

During the operation of the indoor unit 72 in the heating mode, the electric resistance wires of the ceramic heaters 64 are heated so that the fin arrangements 66 are also heated. This heating process activates platinum group metal in the catalyst layers 69, and also separates the odor components from activated alumina in the catalyst layers 69. Activated platinum group metal exhibits an effective catalytic function which oxidizes and decomposes the odor components into odorless substances. Accordingly, the odor components are removed from activated alumina so that an odor-absorbing ability of activated alumina is recovered. In addition, the odor components separated from activated alumina are converted into odorless substances. The air drawn into the indoor unit 72 encounters the heated catalyst layers 69 in the deodorant equipments 63a and 63b so that odor components of the air are converted into odorless substances by the catalytic function of platinum group metal in the catalyst layers 69.

When the heating mode of operation of the indoor unit 72 terminates (the step 303), the ceramic heaters 64 in the deodorant equipments 63a and 63b are de-energized (the step 304). Then, the step 301 is executed again.

When the main power supply switch of the air conditioner is moved to the on position and then the indoor unit 72 is operated in the dehumidifying mode (the step 305), the ceramic heaters 64 in the deodorant equipments 63a and 63b are energized (the step 302).

During the operation of the indoor unit 72 in the dehumidifying mode, the electric resistance wires of the ceramic heaters 64 are heated so that the fin arrangements 66 are also heated. This heating process activates platinum group metal in the catalyst layers 69, and also separates the odor components from activated alumina in the catalyst layers 69. Activated platinum group metal exhibits an effective catalytic function which oxidizes and decomposes the odor components into odorless substances. Accordingly, the odor components are removed from activated alumina so that an odor-absorbing ability of activated alumina is recovered. In addition, the odor components separated from activated alumina are converted into odorless substances. The air drawn into the indoor unit 72 encounters the heated catalyst layers 69 in the deodorant equipments 63a and 63b so that odor components of the air are converted into odorless substances by the catalytic function of platinum group metal in the catalyst layers 69.

When the dehumidifying mode of operation of the indoor unit 72 terminates (the step 303), the ceramic heaters 64 in the deodorant equipments 63a and 63b are de-energized (the step 304). Then, the step 301 is executed again.

When the main power supply switch of the air conditioner is moved to the on position and then the indoor unit 72 is operated in the cooling mode (the step 306), the fan 76 draws air into the indoor unit 72 from the rooms 80a and 80b via the branches 79a and 79b of the intake duct 79.

During the operation of the indoor unit 72 in the cooling mode, when the air is driven through the branches 79a and 79b of the intake duct 79, the air encounters the catalyst layers 69 of the deodorant equipments 63a and 63b so that odor components of the air are absorbed by activated alumina in the catalyst layers 69. Thus, the air is deodorized. Activated alumina forms carriers which provide a porous structure of the catalyst layers 69. Basic material is carried on the carriers so that acid substances are absorbed by the catalyst layers 69.

When the cooling mode of operation of the indoor unit 72 terminates (the step 307), the period "tc" measured by the timer 89 is reset (the step 308) and then the timer 89 is started. Accordingly, the timer 89 commences the time measuring process. Then, the ceramic heaters 64 are energized (the step 309). The electric resistance wires of the ceramic heaters 64 are thus heated so that the fin arrangements 66 are also heated. This heating process activates platinum group metal in the catalyst layers 69, and also separates the odor components from activated alumina in the catalyst layers 69. Activated platinum group metal exhibits an effective catalytic function which oxidizes and decomposes the odor components into odorless substances. Accordingly, the odor components are removed from activated alumina so that an odor-absorbing ability of activated alumina is recovered. In addition, the odor components separated from activated alumina are converted into odorless substances. The air drawn into the indoor unit 72 encounters the heated catalyst layers 69 in the deodorant equipments 63a and 63b so that odor components of the air are converted into odorless substances by the catalytic function of platinum group metal in the catalyst layers 69.

When the period "tc" measured by the timer 89 reaches the given period "Tc" (the step 310), the ceramic heaters 64 are de-energized (the step 311). Then, the step 301 is executed again.

As previously described, in the deodorant equipment 63 of FIGS. 18 and 19, the vitreous coating film 67 covers at least a part of outer surfaces of the fin arrangement 66 through which the ceramic heater 64 extends. The catalyst layer 69 formed on the vitreous coating film 67 contains at least activated alumina, silica, and platinum group metal. While the ceramic heater 64 remains de-energized, activated alumina mainly absorbs stinking acid substances. Thus, a stinking-substance absorbing process is executed. When the ceramic heater 64 is energized, the stinking substances are separated from activated alumina and are decomposed by the catalytic function of platinum group metal in the catalyst layer 69 so that the odor-absorbing ability of activated alumina is recovered. Thus, an absorbing-ability recovering process is executed. The stinking-substance absorbing process and the absorbing-ability recovering process are cyclically and periodically reiterated so that stinking substances can be removed from air for a long time.

The catalyst layer 69 uses silica as an inorganic binder. Therefore, a bonding force of the carrier for activated alumina is increased so that an adequate stiffness of the catalyst layer 69 is attained without decreasing a catalyst activity.

The fin arrangement 66 includes a rectangular base which covers the ceramic heater 64. The fin arrangement 66 also includes radiators 65 projecting outward from the rectangular base thereof. The catalyst layer 69 is provided on the outer surfaces of the fin arrangement 66 including the projecting radiators 65, so that a large total area of the outer surfaces of the catalyst layer 69 is attained without increasing the size of the ceramic heater 64. The fin arrangement 66 protects the ceramic heater 64.

As previously described, the fin arrangement 66 is made of aluminum. The aluminum fin arrangement 66 has a good thermal conductivity, enabling the catalyst layer 69 to be efficiently heated by the ceramic heater 64. The fin arrangement 66 is made by extrusion molding, and hence easy change of the shape of the fin arrangement 66 is enabled in the designing of the fin arrangement 66.

The protective layers 68 are formed on the ends of the fin arrangement 66 and the vitreous coating film 67 in the length direction (the longitudinal direction) of the fin arrangement 66. It is difficult to form the vitreous coating film 67 on the ends of the fin arrangement 66 in the length direction (the longitudinal direction) thereof. Thus, the ends of the fin arrangement 66 tend to be uncovered from the vitreous coating film 67. The protective layers 68 cover the ends of the fin arrangement 66, and prevent the ends of the fin arrangement 66 from being corroded by the catalyst layer 69.

After the cooling mode of operation of the air conditioner terminates, the ceramic heaters 64 are energized. Thus, energization of the ceramic heaters 64 is unexecuted and discharge of hot air from the indoor unit 72 is prevented during the execution of the cooling mode of operation of the air conditioner.

During the operation of the air conditioner in the heating mode, the ceramic heaters 64 remain energized so that the temperature of air discharged from the indoor unit 72 can be increased. Also, during the operation of the air conditioner in the dehumidifying mode, the ceramic heaters 64 remain energized so that a reduction in the temperature of air discharged from the indoor unit 72 can be suppressed.

The deodorant equipments 63a and 63b disposed in the branches 79a and 79b of the intake duct 79 remove stinking components from air drawn into the indoor unit 72 from the rooms 80a and 80b. Since air flowing between the rooms 80a and 80b via the branches 79a and 79b of the intake duct 79 is processed by the deodorant equipments 63a and 63b, it is possible to suppress the occurrence of stinking substances caused by a mixture of odor components of air in the room 80a and odor components of air in the room 80b.

Since the shape of the ceramic heaters 64 can be selected from various shapes, a high degree of freedom in attachment of the deodorant equipments 63a and 63b to the air conditioner is attained.

What is claimed is:

1. A deodorant equipment for an air conditioner, comprising:
    a heater;
    heat conducting means for conducting heat from the heater, said heat conducting means comprising a fin secured to and covering at least a part of an effective heating area of a surface of the heater and having at least one radiator portion extending from the heater along first and second directions, said first direction being perpendicular to a longitudinal direction of the heater, said second direction being parallel to the longitudinal direction of the heater;
    a vitreous coating film covering at least a part of an outer surface of the fin; and
    a catalyst layer provided on said vitreous coating film, said catalyst layer including an absorption member and a catalyst, the absorption member absorbing odor components of air and releasing the odor components when heated, the catalyst oxidizing and decomposing odor components when heated.

2. The deodorant equipment of claim 1, wherein the heater comprises a metal tube heater including an electric resistance member.

3. The deodorant equipment of claim 1, wherein the heater comprises a glass tube heater including an electric resistance member.

4. The deodorant equipment of claim 1, wherein the heater comprises a ceramic heater including an electric resistance member.

5. The deodorant equipment of claim 1, wherein the fin is comprised of aluminized steel.

6. The deodorant equipment of claim 1, wherein the fin is comprised of aluminum.

7. The deodorant equipment of claim 1, wherein the fin is attached to the heater and is formed with the radiator portion by a pressing and deforming process.

8. The deodorant equipment of claim 7, wherein the radiator portion comprises first and second radiators extending in opposite directions respectively.

9. The deodorant equipment of claim 1, wherein the radiator portion extends along a direction of an air flow.

10. The deodorant equipment of claim 1, wherein the radiator portion has first and second radiators projecting in an upstream side and a downstream side with respect to an air flow respectively.

11. The deodorant equipment of claim 10, wherein an angular positional relation between the first radiator and the second radiator corresponds to an angular relation between a direction of a portion of the air flow in the upstream side and a direction of a portion of the air flow in the downstream side.

12. The deodorant equipment of claim 1, wherein the vitreous coating film has a laminate of a lower layer and an upper layer.

13. The deodorant equipment of claim 1, wherein the catalyst layer comprises at least activated alumina, silica, and platinum group metal.

14. The deodorant equipment of claim 1, wherein the catalyst layer comprises at least activated alumina, silica, zeolite, and platinum group metal.

15. The deodorant equipment of claim 1, wherein the catalyst layer has a laminate of an inner layer and an outer layer each including a platinum group metal, a concentration of platinum group metal being higher in said outer layer than in said inner layer.

16. The deodorant equipment of claim 1, further comprising:
    insulating caps provided on ends of the heater;
    a heat insulating plate secured to the heater to thermally shield a heating portion of the heater;
    an attachment device fixing the heater and the heat insulating plate via the insulating caps; and
    a temperature-responsive breaker located on the heat insulating plate and electrically connected in series with the heater.

17. The deodorant equipment of claim 16, wherein the temperature-responsive breaker comprises a bimetal.

18. The deodorant equipment of claim 16, wherein the temperature-responsive breaker comprises a series combination of a bimetal and a fuse.

19. The deodorant equipment of claim 16, wherein the heater has a bent end.

20. The deodorant equipment of claim 1, further comprising:
   operation detecting means for detecting operation and suspension of an indoor unit of the air conditioner;
   a first timer performing a time measuring process in response to an output signal of the operation detecting means during operation of the indoor unit, the first timer resetting a total operation time of the indoor unit and outputting a signal when the total operation time reaches a given time; and
   a second timer outputting a signal to the heater to energize the heater for a given time in response to the output signal of the first timer.

21. The deodorant equipment of claim 1, further comprising:
   operation detecting means for detecting operation and suspension of an indoor unit of the air conditioner;
   operation mode detecting means for detecting heating operation and cooling operation of the air conditioner;
   heating operation detecting means for detecting start and stop of the heating operation in response to an output signal of the operation detecting means and a heating operation signal outputted from the operation mode detecting means;
   a first timer performing a time measuring process in response to an output signal of the heating operation detecting means during the heating operation of the indoor unit, the first timer resetting a total heating operation time of the indoor unit and outputting a signal when the total heating operation time reaches a given time;
   cooling operation end detecting means for detecting an end of the cooling operation in response to the output signal of the operation detecting means and a cooling operation signal outputted from the operation mode detecting means; and
   a second timer outputting a signal to the heater to energize the heater for a given time in response to one of an output signal of the cooling operation end detecting means and the output signal of the first timer.

22. The deodorant equipment of claim 1, further comprising:
   operation detecting means for detecting operation and suspension of an indoor unit of the air conditioner;
   operation mode detecting means for detecting heating operation, cooling operation, and dehumidifying operation of the air conditioner;
   heating operation detecting means for detecting start and stop of the heating operation, and outputting a signal during the heating operation in response to an output signal of the operation detecting means and a heating operation signal outputted from the operation mode detecting means;
   cooling operation end detecting means for detecting an end of the cooling operation in response to the output signal of the operation detecting means and a cooling operation signal outputted from the operation mode detecting means;
   dehumidifying operation detecting means for start and stop of the dehumidifying operation, and outputting a signal during the dehumidifying operation in response to the output signal of the operation detecting means and a dehumidifying operation signal outputted from the operation mode detecting means;
   a timer outputting a signal for a given time in response to the output signal of the cooling operation end detecting means; and
   energizing means for outputting a signal to the heater to energize the heater in response to the output signal of the heating operation detecting means, the output signal of the dehumidifying operation detecting means, and an output signal of the timer.

23. The deodorant equipment of claim 1, further comprising:
   sensing means for detecting an odor in a room;
   a fan disposed in an indoor unit of the air conditioner and circulating air in the room;
   operation detecting means for detecting operation and suspension of the indoor unit which includes sole operation of the fan;
   fan control means responsive to an output signal of the sensing means and a stop signal outputted from the operation detecting means for activating the fan when the sensing means detects an odor in the room during suspension of the indoor unit;
   a first timer performing a time measuring process in response to an operation signal outputted from the operation detecting means during the operation of the indoor unit, the first timer resetting a total operation time of the indoor unit and outputting a signal when the total operation time reaches a given time; and
   a second timer outputting a signal to the heater to energize the heater for a given time in response to the output signal of the first timer.

24. A deodorizing apparatus comprising:
   a heater;
   a heat conducting means for conducting heat from the heater, said heat conducting means comprising a fin secured to and covering at least a part of an effective heating area of a surface of the heater and having at least one radiator portion extending from the heater along first and second directions, said first direction being perpendicular to a longitudinal direction of the heater, said second direction being parallel to the longitudinal direction of the heater;
   an absorbent for absorbing odor components of air, and releasing the absorbed odor components when being heated; and
   a catalyst for decomposing the odor components released from the absorbent.

25. The deodorizing apparatus of claim 24, further comprising means connected to the heater for periodically activating the heater.

26. An air conditioner having a deodorizing apparatus incorporated therein, comprising:
   means for detecting whether or not the air conditioner is operating;
   absorbent for absorbing odor components of air, and releasing the absorbed odor components when being heated;
   a catalyst for decomposing the odor components released from the absorbent; and
   means connected to the detecting means for periodically heating the absorbent while the detecting means continues to detect that the air conditioner is operating wherein said means connected to the detecting means for periodically heating the absorbent comprises a heater and heat conducting means for conducting heat from the heater, said heat conducting means comprising a fin secured to and covering at least part of an effective heating area of a surface of the heater and having at least one radiator portion extending from the heater along first and second directions, said first direction being perpendicular to a longitudinal direction of the heater, said second direction being parallel to the longitudinal direction of the heater.

27. The deodorizing apparatus of claim 26, further comprising:
second detecting means for detecting whether or not the air conditioner is operating in a cooling mode; and
means connected to the second detecting means and the heating means for preventing the heating means from heating the absorbent when the second detecting means detects that the air conditioner is operating in the cooling mode.

28. An air conditioner having a deodorizing apparatus incorporated therein, comprising:
means for detecting a change of operation of the air conditioner from a cooling mode;
absorbent for absorbing odor components of air, and releasing the absorbed odor components when being heated;
a catalyst for decomposing the odor components released from the absorbent; and
means connected to the detecting means for heating the absorbent after the detecting means detects a change of operation of the air conditioner from the cooling mode wherein said means connected to the detecting means for periodically heating the absorbent comprises a heater and heat conducting means for conducting heat from the heater, said heat conducting means comprising a fin secured to and covering at least part of an effective heating area of a surface of the heater and having at least one radiator portion extending from the heater along first and second directions, said first direction being perpendicular to a longitudinal direction of the heater, said second direction being parallel to the longitudinal direction of the heater.

29. The air conditioner of claim 26, further comprising a vitreous coating film covering at least a part of an outer surface of the fin, wherein the catalyst is provided on the vitreous coating film.

30. The air conditioner of claim 28, further comprising a vitreous coating film covering at least a part of an outer surface of the fin, wherein the catalyst is provided on the vitreous coating film.

31. The deodorant equipment of claim 1, wherein said at least one radiator portion is substantially planar.

32. The deodorant equipment of claim 24, wherein said at least one radiator portion is substantially planar.

33. A deodorant equipment for an air conditioner, comprising:
a heater;
a fin covering at least a part of an effective heating area of a surface of the heater and having at least one radiator portion extending along a longitudinal direction of the heater, said fin comprising a metal tube;
a vitreous coating film covering at least a part of an outer surface of the fin; and
a catalyst layer provided on said vitreous coating film, said catalyst layer including an absorption member and a catalyst, the absorption member absorbing odor components of air and releasing the odor components when heated, the catalyst oxidizing and decomposing odor components when heated.

34. The deodorant equipment of claim 33, wherein the metal tube has adjacent and opposing edges welded together.

35. The deodorant equipment of claim 34, wherein a space is provided between the fin and the heater, the space extending along a direction parallel to the longitudinal direction of the fin, the adjacent and opposing edges facing said space.

36. A deodorant equipment for an air conditioner, comprising:
a heater;
a fin covering at least a part of an effective heating area of a surface of the heater and having at least one radiator portion extending along a longitudinal direction of the heater;
a vitreous coating film covering at least a part of an outer surface of the fin;
a catalyst layer provided on said vitreous coating film, said catalyst layer including an absorption member and a catalyst, the absorption member absorbing odor components of air and releasing the odor components when heated, the catalyst oxidizing and decomposing odor components when heated; and
protective layers provided on opposite longitudinal ends of the fin, the protective layers preventing the catalyst layer from directly contacting the fin.

* * * * *